US006703227B2

(12) United States Patent
Jakel et al.

(10) Patent No.: US 6,703,227 B2
(45) Date of Patent: Mar. 9, 2004

(54) METHOD FOR PRODUCING FERMENTATION-BASED PRODUCTS FROM HIGH OIL CORN

(75) Inventors: Neal Torrey Jakel, Lake Zurich, IL (US); James F. Ulrich, Highwood, IL (US)

(73) Assignee: Renessen LLC, Bannockburn, IL (US)

( * ) Notice: Subject to any disclaimer, the term of this patent is extended or adjusted under 35 U.S.C. 154(b) by 0 days.

(21) Appl. No.: 10/369,171

(22) Filed: Feb. 18, 2003

(65) Prior Publication Data

US 2003/0194788 A1 Oct. 16, 2003

Related U.S. Application Data

(63) Continuation-in-part of application No. 09/927,836, filed on Aug. 10, 2001, which is a continuation-in-part of application No. 09/637,843, filed on Aug. 10, 2000, which is a continuation-in-part of application No. 09/249,280, filed on Feb. 11, 1999, now Pat. No. 6,313,328.

(51) Int. Cl.$^7$ .................................. C12P 19/00
(52) U.S. Cl. .................. 435/72; 435/144; 435/157; 435/161; 435/162
(58) Field of Search .................. 435/157, 161, 435/162, 144, 72

(56) References Cited

U.S. PATENT DOCUMENTS

| | | |
|---|---|---|
| 3,432,529 A | 3/1969 | Demper |
| 3,519,431 A | 7/1970 | Wayne |
| 3,786,078 A | 1/1974 | Finley et al. |
| 3,909,288 A | 9/1975 | Powell et al. |
| 3,939,281 A | 2/1976 | Schwengers |
| 4,008,210 A | 2/1977 | Steele et al. |
| 4,246,184 A | 1/1981 | Pressick et al. |
| 4,277,411 A | 7/1981 | Yahl |

(List continued on next page.)

FOREIGN PATENT DOCUMENTS

| | | |
|---|---|---|
| EP | 0623100 B1 | 4/1997 |
| GB | 2269084 A | 2/1994 |
| GB | 2309150 A | 7/1997 |
| WO | WO 94/15483 A1 | 7/1994 |
| WO | WO 95/22598 A2 | 8/1995 |
| WO | WO 98/43473 A1 | 10/1998 |
| WO | WO 99/52376 A1 | 10/1999 |
| WO | WO 00/47702 A1 | 8/2000 |
| WO | WO 01/55283 A1 | 8/2001 |
| WO | WO 02/13624 A1 | 2/2002 |
| WO | WO 02/14459 A2 | 2/2002 |

OTHER PUBLICATIONS

Aguilera et al., "Laboratory and Pilot Solvent Extraction of Extruded High–Oil Corn," *JACOS*, 1986, 63(2): pp. 239–243, Texas A&M University, College Station, Texas, USA.

Bockisch, Michael, "Fats and Oils Handbok," 1993, pp. 344, 345 & 360–391, Hamburg, Germany.

Midwest Research Institute For The Office Of Air Quality And Planning And Standards, Emission Factor Documentation for AP–42, Section 9.11.1, "Vegetable Processing," Final Report, Nov. 1995, p. 2–12, Research Triangle Park, North Carolina, USA.

(List continued on next page.)

*Primary Examiner*—Deborah Carr
(74) *Attorney, Agent, or Firm*—Leydig, Voit & Mayer, Ltd.

(57) ABSTRACT

Corn oil and corn meal obtained from high oil corn are included in useful products. A method of producing fermentation-based products comprising combining corn meal remaining after the extraction of oil from whole high oil corn with water and an enzyme. This combination is incubated and then mixed with a micro-organism capable of fermenting a carbon source to produce fermentation-based products such as ethanol.

21 Claims, 6 Drawing Sheets

U.S. PATENT DOCUMENTS

| | | | |
|---|---|---|---|
| 4,310,468 | A | 1/1982 | Reiners |
| 4,341,713 | A | 7/1982 | Stolp et al. |
| 4,442,034 | A | 4/1984 | Suzuki et al. |
| 4,456,556 | A | 6/1984 | Grimsby |
| 4,456,557 | A | 6/1984 | Grimsby |
| 4,486,353 | A | 12/1984 | Matsuzaki et al. |
| 4,495,207 | A | 1/1985 | Christianson et al. |
| 4,594,260 | A | 6/1986 | Vaqueiro et al. |
| 5,035,910 | A | 7/1991 | Jones et al. |
| 5,085,808 | A | 2/1992 | Snyder et al. |
| 5,320,669 | A | 6/1994 | Lim et al. |
| 5,408,924 | A | 4/1995 | Arendt et al. |
| 5,525,746 | A | 6/1996 | Franke |
| 5,670,678 | A | 9/1997 | Rothbart |
| 5,675,065 | A | 10/1997 | Bergquist |
| 5,706,603 | A | 1/1998 | Bergquist et al. |
| 5,750,851 | A | 5/1998 | Geadelmann et al. |
| 5,851,572 | A | 12/1998 | Cook et al. |
| 5,908,940 | A | 6/1999 | Lane et al. |

OTHER PUBLICATIONS

Watson, "Corn and Corn Improvement," *Marketing, Processing and Utilization*, 3rd Edition, 1988, No. 18 series Agronomy, pp. 917–918, Madison, Wisconsin, USA.

Watson et al., "Structure and Composition" *Corn: Corn Chemistry and Technology*, 1987, pp. 538–539, St. Paul, Minnesota, USA.

Blessin, "Carotenoids of Corn and Sorghum," *Cereal. Chem.*, 59:236–242 (1962).

Blessin et al., "Carotenoids of Corn and Sorghum," *Cereal Chem.*, 40:582–586 (1963).

Grams et al., "Distribution of Tocopherols Within The Corn Kernel," *J. Amer. Oil Chemists Soc.*, 47:337–339 (1970).

Lambert, "High–Oil Corn Hybrids," *Specialty Corns*, pp. 123–145 (1994).

Paulis et al., "Selection of High–Lysine Corns with Varied Kernel Characteristics and Compositions of a Rapid Turbidimetric assay for Zein," *J. Agr. Food Chem.*, 22:318–323 (1974).

AOCS Recommended Practice Ba 2b–82 (1997).

AOCS Recommended Practice Ba 4e–93 (1999).

AOCS Recommended Practice Ba 6–84 (1997).

AOCS Recommended Practice Ba 3–38 (1997).

AOCS Recommended Practice Ca 5a–40 (1997).

AOCS Official Method Ca 12–55 (1997).

AOCS Official Method Cc 13b–45 (2000).

Standard Analytical Methods of the Member Companies of the Corn Refiners Association, Inc., Standard 6–3–57 (1986).

XP–002199802, DuPont Quality Grains (1996).

METHOD FOR PRODUCING FERMENTATION-BASED PRODUCTS FROM HIGH OIL CORN

The present application is a continuation-in-part of U.S. patent application Ser. No. 09/927,836, filed Aug. 10, 2001, which was a continuation-in-part of application Ser. No. 09/637,843, filed Aug. 10, 2000, which was a continuation-in-part of application Ser. No. 09/249,280, filed Feb. 11, 1999 now U.S. Pat. No. 6,313,328, the entire disclosures of which are hereby incorporated by reference.

FIELD OF THE INVENTION

The present invention relates to a method for producing fermentation-based products that are derived from corn having an oil content of about 6 percent by weight or more.

BACKGROUND OF THE INVENTION

Corn, *Zea mays L.*, is grown for many reasons including its use in food and industrial applications. Corn oil and corn meal are two of many useful products derived from corn.

Commercial processing plants utilizing conventional methods for extracting corn oil from conventional corn separate the corn seed into its component parts, e.g., endosperm, germ, tipcap, and pericarp, and then extract corn oil from the corn germ fraction. Corn germ produced by wet or dry milling is processed either by pressing the germ to remove the oil or by flaking the germ and extracting the oil with a solvent. In both processes, because the germ was separated from the remainder of the kernel, many or all of the valuable components of the endosperm fraction are absent from the oil.

Ethanol (ethyl alcohol, grain alcohol, EtOH) is a clear, colorless liquid with a characteristic, agreeable odor that is desirable for use in motor vehicle fuels to control pollution. Traditionally, corn has been used, along with other crops such as sugar beets and sugar cane, to produce ethanol.

Corn has traditionally been processed by one of two methods. The wet milling process involves soaking or steeping the corn to recover the oil prior to processing, leaving behind a corn meal. In the dry milling process, the whole kernel may be ground and then water is added to form a mash. In either case, where the corn is to be used to produce ethanol, the meal or mash is treated with an enzyme such to convert the starch contained in the corn to sugars. The enzyme treated mash or meal is then fermented using yeast. The yeast converts the sugar to ethanol and carbon dioxide. Once the ethanol and carbon dioxide have been separated, such as by distillation, the remaining non-fermentable part of the corn can be processed to recover other nutrients and can also be processed into animal feed.

Industry advocates are continually in search of better corn-based feedstocks. One particularly valuable feedstock is corn meal produced from high oil corn.

BRIEF SUMMARY OF THE INVENTION

Finished products are advantageously produced using high oil corn having an oil content of about 6 percent by weight or greater. Some embodiments of the invention include those wherein: 1) the corn meal has a fiber content of about 3%, a starch content of about 65%, and a protein content of about 12%, at a moisture content of about 10%; 2) the high oil corn grain has a total oil content of at least about 6 percent by weight, at least about 7 percent by weight, at least about 8 percent by weight; at least about 10 percent by weight, at least about 12 percent by weight, at least about 14 percent by weight, or from about 7 percent by weight to about 30 percent by weight; 3) the corn grain being flaked is whole corn grain or cracked corn grain; 4) the corn grain has been subjected to an oil extraction process such as solvent extraction, hydraulic pressing, or expeller pressing, aqueous and enzyme extraction; 5) the high oil corn grain has a total protein content of at least about 7 percent by weight, at least about 9 percent by weight, at least about 11 percent by weight, or from about 7 percent by weight to about 20 percent by weight; 6) the high oil corn grain has a total lysine content of at least about 0.15 percent by weight, at least about 0.5 percent by weight, or from about 0.25 percent by weight to about 2.0 percent by weight; and/or 7) the high oil corn grain has a total tryptophan content of at least about 0.03 percent by weight, at least about 0.20 percent by weight, or from about 0.03 percent by weight to about 2.0 percent by weight.

A preferred embodiment provides a method of obtaining corn oil and solvent extracted corn meal (SEC) from high oil corn. The method provides steps of: 1) tempering the corn; 2) cracking the tempered corn; 3) conditioning the cracked corn; 4) flaking the conditioned corn; 5) extracting the flaked corn; and 6) removing the solvent from both the corn oil and solvent extracted corn meal. The method provides a greater overall content of corn oil and concentrates the proteins in the meal. Moreover, solvent extractable pigments can be removed from the SEC.

Other embodiments of the invention include those wherein: 1) high oil corn grain is cracked, conditioned, flaked and extracted with a solvent; 2) the high oil corn grain has a total oil content of at least about 6 percent by weight, at least about 7 percent by weight, at least about 8 percent by weight; at least about 10 percent by weight, at least about 12 percent by weight, at least about 14 percent by weight, or from about 7 percent by weight to about 30 percent by weight; 3) the corn oil is extracted by pressing cracked corn; 4) the corn oil is extracted by subjecting flaked corn grain to a solvent-based extraction process; 5) the solvents used to extract miscible or soluble substances from the flaked grain include all forms of commercially available hexanes, isopropyl alcohol, ethanol, supercritical carbon dioxide or mixtures thereof; 6) the extracted corn oil is provided as miscella; 7) the corn oil is refined by additional processing; and 8) the corn oil is extracted by subjecting flaked corn grain to hydraulic pressing and/or expeller pressing, aqueous and/or enzyme extraction processes.

Another aspect of the invention provides a method of using extracted corn oil as a feedstock in an oil refining process. The method comprises the steps of: 1) providing an extracted crude corn oil obtained by at least flaking high oil corn to form flaked corn and extracting the flaked corn to remove a portion of the corn oil therefrom and form the extracted crude corn oil; and 2) including the extracted crude corn oil in a raw material stream of an oil refining process.

Yet another aspect of the invention provides various methods of forming extracted blended meals. A first embodiment of this aspect of the invention provides a method of forming an extracted blended meal comprising an extracted meal obtained from high oil corn and one or more other oilseed meals, the method comprising the step of: 1) combining high oil corn grain and one or more other oilseed grains to form a grain mixture; and 2) subjecting the grain mixture to flaking and an extraction process to remove oil therefrom and form the extracted blended meal. A second embodiment provides a method comprising the steps of: 1) combining a cracked and conditioned high oil corn with another cracked and conditioned oilseed to form a conditioned mixture; 2) flaking the conditioned mixture to form a flaked mixture; and 3) subjecting the flaked mixture to an extraction process to remove oil therefrom and form the extracted blended meal. A third embodiment provides a method comprising the steps of: 1) combining a cracked, conditioned and flaked high oil corn with a cracked, conditioned and flaked other oilseed to form a flaked mixture; and 2) subjecting the flaked mixture to an extraction process to remove oil therefrom and form the extracted blended meal. A fourth embodiment provides a method comprising the step of combining an extracted corn meal with one or more extracted other oilseed meals to form a blended meal, wherein the extracted corn meal has been obtained by at least flaking and extracting high oil corn to form the extracted corn meal. A fifth embodiment provides a blended extracted meal product prepared according to any one of the above-described methods.

In addition, the present invention provides a method of producing fermentation-based products, such as ethanol and citric acid, from high oil corn. The method comprises 1) combining an enzyme, water, and a corn meal produced from high oil corn grain, wherein the oil has been extracted from the high oil corn grain; 2) incubating the combination; and 3) mixing the combination with a micro-organism capable of fermenting a carbon source to produce fermentation-based products. The enzyme is any enzyme suitable for fermentation of high oil corn, including an amylase, a protease, a cellulase, an esterase and a liginase. The high oil corn can be optionally tempered, flaked, conditioned and/or cracked in order to obtain the corn meal.

Unless otherwise defined, all technical and scientific terms and abbreviations used herein have the same meaning as commonly understood by one of ordinary skill in the art to which this invention pertains. Although methods and materials similar or equivalent to those described herein can be used in the practice of the present invention, suitable methods and materials are described below without intending that any such methods and materials limit the invention described herein. All patents, publications and official analytical methods referred to herein are incorporated by reference in their entirety. Additional features and advantages of the invention will be apparent from the following description of illustrative embodiments of the invention and from the claims.

DETAILED DESCRIPTION OF THE INVENTION

Figure 1:
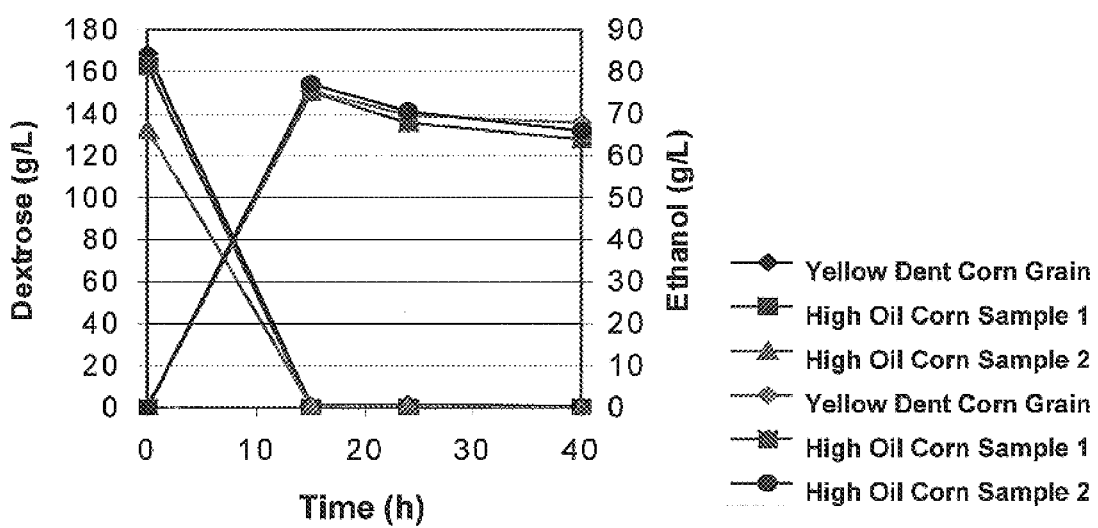
FIG. 1 illustrates the total amount of ethanol produced and dextrose consumed by yeast grown on yellow dent corn grain and high oil corn grain with equalized weight.

It has been discovered that corn oil can be rapidly and efficiently extracted on a commercial-scale from corn grain having increased oil content by optionally cracking and then conditioning, and flaking the corn grain and extracting a corn oil. Useful corn grain for the novel flaking oil processing method has a total oil content greater than about 6 percent by weight. Increases in the oil content of corn grain may increase flaking efficiency during processing. Suitable flaking equipment and methods include conventional flaking equipment and methods used for flaking soybean and other similar oilseed types. Suitable extracting equipment and methods may include conventional methods used for extracting oil from soybean flakes and other similar oilseed types.

High oil corn seed or "grain" harvested from any of several different types of corn plants is useful in the invention. These types of corn plants are, for example, hybrids, inbreds, transgenic plants, genetically modified plants or a specific population of plants. Enhanced extracted meals can be made by subjecting enhanced high oil corn to the extraction process described herein. Useful corn grain types include, for example, flint corn, popcorn, flour corn, dent corn, white corn, and sweet corn. The high oil corn grain can be in any form including whole corn, cracked corn, or other processed corn or parts thereof that are amenable to flaking but different from the standard methods of germ separation employed in dry and wet milling for subsequent recovery of oil from the germ.

As used herein, the terms "whole kernel" or "whole corn" mean a kernel that has not been separated into its constituent parts, e.g. the hull, endosperm, tipcap, pericarp, and germ have not been purposefully separated from each other. The whole corn may or may not have been ground, crushed, cracked, flaked, or abraded. Purposeful separation of one corn constituent from another does not include random separation that may occur during storage, handling, transport, crushing, flaking, cracking, grinding or abrading. A purposeful separation of the constituent part is one wherein at least 50% of one constituent, e.g., germ, has been separated from the remaining constituents.

As used herein, the term "high oil corn" refers to corn grain comprising at least about 6 percent by weight or greater, preferably at least about 7 percent by weight or greater, and preferably at least about 8 percent by weight or greater oil. A high oil corn has an elevated level of oil as compared to conventional yellow dent corn, which has an oil content of about 3 percent by weight to about 5 percent by weight. Additionally, the total oil content of corn grain suitable for the invention can be, for example, grain having an oil content at least about 9 percent by weight, at least about 11 percent by weight, at least about 12 percent by weight, at least about 15 percent by weight, at least about 18 percent by weight, at least about 20 percent by weight, from about 8 percent by weight to about 20 percent by weight oil, from about 10 percent by weight to about 30 percent by weight oil, or from about 14 percent by weight to about 30 percent by weight, and values within those ranges. Although the oil content can be determined at any moisture content, it is acceptable to normalize the oil content to a moisture content of about 15.5%.

High oil corn useful in making the oil and meal described herein are available from Cargill, Incorporated (Minneapolis, Minn.) or Pfister Hybrid Corn Co. (El Paso, Ill.). Other suitable high oil corn includes the corn populations known as Illinois High Oil (IHO) and Alexander High Oil (Alexo), samples of which are available from the University of Illinois Maize Genetics Cooperative—Stock Center (Urbana, Ill.).

Corn grain having an elevated total oil content is identified by any of a number of methods known to those of ordinary skill in the art. The oil content of grain, including the fat content of a meal extracted from the grain, can be determined using American Oil and Chemical Society Official Method, 5$^{th}$ edition, March 1998, ("AOCS method Ba 3-38"). AOCS method Ba 3–38 quantifies substances that are extracted by petroleum ether under conditions of the test. The oil content or concentration is the weight percentage of the oil with respect to the total weight of the seed sample. Oil content may be normalized and reported at any desired moisture basis.

Other suitable methods for identifying high oil corn grain are described herein. According to one method, corn ears are selected using a near infrared (NIR) oil detector to select corn ears having corn kernels with elevated oil levels. Likewise, an NIR detector can also be used to select individual corn kernels having elevated levels of corn oil. However, selecting individual ears and/or kernels having elevated oil content may not be cost effective in identifying high oil kernels suitable for processing using methods described herein. Generally, corn seed producing corn plants that yield grain having elevated total oil concentrations is planted and harvested using known farming methods. Methods for developing corn inbreds, hybrids, transgenic species and populations that generate corn plants producing grain having elevated oil concentrations are known and described in Lambert (Specialty Corn, CRC Press Inc., Boca Raton, Fla., pp. 123–145 (1994).

One of the suitable high oil corns used as a raw material for preparing the corn oil and corn meal used in the invention has a nutrient profile as shown in Table 1. Amounts are expressed on an "as is" or "as fed" moisture level. Protein, oil, and starch levels can vary in a number of possible combinations in the high oil corn used as a raw material for meal and oil used in the invention. Acceptable amounts of moisture, oil, protein, starch, lysine, and tryptophan are illustrated in Table 1. However, additional combinations, such as 12 percent by weight protein and 12 percent by weight oil, not shown as indicated amounts in the table are within the scope and range of corn grain to be used to produce oil and meal used in the invention.

TABLE 1

| Component | Amount 1 (percent by weight) | Amount 2 (percent by weight) | Amount 3 (percent by weight) | General Amount (percent by weight) |
|---|---|---|---|---|
| Moisture | 14 | 14 | 14 | 5–45 |
| Oil | 8 | 12 | 20 | 6–30 |
| Protein | 9 | 9 | 17 | 5–20 |
| Starch | 61 | 54 | 41 | 35–80 |
| Lysine | 0.35 | 0.50 | 1.0 | 0.15–2.0 |
| Tryptophan | 0.088 | 0.11 | 0.15 | 0.03–2.0 |

Another suitable high oil corn used as a raw material for preparing the corn oil and corn meal used in the invention has a nutrient profile as shown in Table 2. Amounts are expressed on an "as is" or "as fed" moisture level. The amounts shown in Table 2 are exemplary for a corn grain having 12 percent by weight oil and 9 percent by weight protein.

TABLE 2

| Component | Amount (percent by weight) | General Amount (percent by weight) |
|---|---|---|
| Moisture | 14 | 5–45 |
| Oil | 12 | 6–30 |
| Protein | 9 | 5–20 |
| Starch | 65 | 35–80 |
| Fiber | 3 | 1–5 |
| Ash | 1.18 | 0.59–4.72 |
| Lysine | 0.33 | 0.2–2.0 |
| Tryptophan | 0.09 | 0.03–2.0 |
| Methionine | 0.25 | 0.13–1.00 |
| Total Sulfur Amino Acids | 0.46 | 0.23–1.84 |
| Valine | 0.45 | 0.23–1.80 |
| Isoleucine | 0.34 | 0.17–1.36 |
| Arginine | 0.45 | 0.23–1.80 |
| Threonine | 0.34 | 0.17–1.36 |
| Leucine | 1.03 | 0.52–4.12 |
| Histidine | 0.27 | 0.14–1.08 |
| Phenylalanine | 0.44 | 0.22–1.76 |
| Alanine | 0.70 | 0.35–2.80 |
| Aspartic | 0.74 | 0.37–2.96 |
| Cysteine | 0.22 | 0.11–0.88 |
| Glutamic | 1.9 | 0.95–7.6 |
| Glycine | 0.46 | 0.23–1.84 |
| Proline | 0.86 | 0.43–3.44 |
| Tyrosine | 0.06 | 0.03–0.54 |
| Serine | 0.46 | 0.23–1.84 |

Table 3 shows amino acid levels (based on a corn grain moisture content of about 10%) of two high oil corn grain samples and normal yellow corn grain. The oil and protein levels of high oil corn sample 1 (HOC 1) were 13.3 percent by weight and 10.7 percent by weight respectively, expressed on a dry matter basis. The oil and protein levels of high oil corn sample 2 (HOC 2) were 13.0 percent by weight and 11.2 percent by weight respectively, expressed on a dry matter basis. For comparison, normal yellow corn grain has about 4.2 percent by weight oil and about 9.2 percent by weight protein on a dry matter basis.

TABLE 3

| Amino Acid | HOC 1 (%) | HOC 2 (%) | Yellow Corn (%) |
|---|---|---|---|
| Aspartic Acid | 0.71 | 0.68 | 0.48 |
| Threonine | 0.33 | 0.30 | 0.19 |
| Serine | 0.37 | 0.27 | 0.19 |
| Glutamic Acid | 1.84 | 1.79 | 1.16 |
| Proline | 0.83 | 0.78 | 0.52 |
| Glycine | 0.40 | 0.42 | 0.24 |
| Alanine | 0.77 | 0.74 | 0.47 |
| Valine | 0.51 | 0.52 | 0.33 |
| Cysteine | 0.21 | 0.23 | 0.16 |
| Methionine | 0.46 | 0.47 | 0.39 |
| Isoleucine | 0.30 | 0.30 | 0.20 |
| Leucine | 1.19 | 1.08 | 0.74 |
| Tyrosine | 0.11 | 0.11 | 0.06 |
| Phenylalanine | 0.52 | 0.48 | 0.32 |
| Tryptophan | 0.06 | 0.07 | 0.05 |
| Lysine | 0.34 | 0.38 | 0.21 |
| Histidine | 0.29 | 0.29 | 0.18 |
| Arginine | 0.45 | 0.48 | 0.28 |

High oil corn is generally subjected to an extraction process as described herein to provide the enhanced corn oil and corn meal which may be included in the finished products of the invention or serve as a feedstock for further processing steps such as fermentation for the ultimate production of ethanol. As used herein, the term "finished product" or "product" refers to an article or manufacture made by combining the corn oil and/or corn meal of the invention with a variety of other ingredients. The specific ingredients included in a product will be determined according to the ultimate use of the product. Exemplary products include animal feed, raw material for chemical modification, biodegradable plastic, blended food product, edible oil, cooking oil, lubricant, biodiesel, snack food, cosmetics, and fermentation process raw material. Products incorporating the meal described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multi-vitamin supplements, diet drinks, and cereal foods.

For example, starting with a single corn type (e.g., 12 percent by weight oil and 9 percent by weight protein), more than one corn meal type can be made to meet certain compositional requirements. The significance of this flexibility relates to the nutrient density within feed products. One significant advantage of the use of this type of high oil corn and extraction process is that an extracted corn meal can be made to have a specific oil level depending on the extent of oil extraction. Once the oil is removed from the flakes, the remaining corn meal has a nutrient density for protein, amino acids, and other nutrients not removed by the process, greater or different than normal corn grain and greater than that of the starting corn, e.g., 12 percent by weight oil, 9 percent by weight protein.

According to one extraction process used in preparing the corn oil and corn meal as described herein, whole grain high oil corn is optionally tempered, optionally cracked, and then conditioned and flaked. After flaking, the flaked corn is extracted as described herein.

Whole grain corn is optionally tempered before the extraction process. As used herein, the term "tempering" is used interchangeably with the terms "heat soaking" or "steaming" and is a means to uniformly distribute the added moisture through the entire corn kernel. Any tempering method known in the art is acceptable. In general, the corn is steeped in an appropriate amount of water for any suitable length of time, such as at least 20 min, preferably at least 4 h, preferably at least 6 h, more preferably at least 12 h, or most preferably at least 24 h. After the corn has steeped for the desired length of time, its moisture content is retested. The corn may be stored for short periods, but is preferably processed within 24 h and most preferably processed immediately.

Whole grain corn is also optionally cracked. In a preferred embodiment, the whole high oil corn is cracked after tempering yet before conditioning. The high oil corn may be cracked by passing the whole grain corn between two rollers with corrugated teeth spinning toward each other spaced by a defined gap, and/or passing through a grind mill where a rotating toothed disk spins at an adjustable distance from a stationary disk, and/or the use of a hammermill where two rotating metal "hammer" like devices spinning next to one another. Methods for cracking corn or high oil seeds are described in Watson, S. A. & P. E. Ramstad, ed. (1987, Corn: Chemistry and Technology, Chapter 11, American Association of Cereal Chemist, Inc., St. Paul, Minn.), the disclosure of which is hereby incorporated by reference in its entirety. A "cracked" corn is a corn that has undergone the above-described cracking process.

Regardless of whether or not the corn is cracked, it is conditioned using methods known to those of ordinary skill in the art and/or methods described herein. As used herein, the term "conditioning" refers to a process by which the corn kernel is softened or plasticized to render it more pliable and amenable to the flaking and extraction processes. Conditioning may include the addition of steam (saturated and/or non-saturated steam) and/or water to the high oil corn. This is done by the use of a rotary conditioner. During the steam addition process, both the temperature and the moisture levels are elevated. The temperature ranges between about 140° F. and about 210° F. and the moisture is increased by about 1% to about 15%.

The high oil corn grain is then flaked to any useful size. As used herein, the term "flaking" refers to a process by which corn grain is passed one or more times through flaking rollers to produce flakes. The flaked corn may have a final flake thickness of about $5/1000$ to $100/1000$ of an inch (~0.12 mm to 2.0 mm) or preferably about 0.01 inches (0.25 mm), although other thicknesses may also be used. Useful flake thickness may depend on external limiting parameters such as the oil content of the corn, the moisture content, the corn type, e.g., dent or flint, and the oil extractor type. Suitable methods for flaking high oil corn are detailed herein and in D. R. Erickson, Practical Handbook of Soybean Processing Utilization (1995, AOCS Press), the entire disclosure of which is hereby incorporated by reference. Suitable flaking methods also include those known to those of ordinary skill in the art of oilseed processing.

After the corn is tempered, cracked and/or conditioned and flaked, the flaked corn is subjected to an extraction process to extract oil to form an extracted corn meal (ECM). Corn oil is extracted from flaked grain by one or more extraction steps using any extraction method. Generally, substantially, or about all of the oil is extracted in a single extraction process. Useful extraction methods include solvent extraction, continuous solvent extraction, hydraulic pressing, expeller pressing, aqueous and/or enzyme extraction. Useful solvents for solvent extraction include, for example, all forms of commercially available pentane, hexanes, isopropyl alcohol, ethanol, supercritical carbon dioxide, combinations thereof, and other similar solvents. For example, corn oil can be extracted from flaked grain using a hexane-based solvent extractor. Solvent extractors can include both percolation and immersion type extractors. In a preferred embodiment, a continuous solvent extraction process allows the flaked corn to remain in contact with the solvent for at least 10 min, preferably at least 30 min, more preferably at least 60 min, and most preferably at least 90 min.

Materials removed from solvent-based extractors include wet flakes and miscella. A miscella is a mixture of extracted oil and solvent. The wet flakes are the materials that remain after some or all of the solvent-soluble material has been extracted. Wet flakes also contain a quantity of solvent. Solvent is reclaimed from both the miscella and wet flakes using methods such as rising film evaporation, or drying, and raising the temperature using equipment such as flash tanks and/or de-solventiser/toasters. For example, heat is applied to the wet flakes or miscella under atmospheric pressure, under elevated pressure, or under vacuum to evaporate the solvent. The evaporated solvent is then condensed in a separate recovery system, and optionally dewatered and recycled to the extractor.

Desolventized miscella is commonly termed crude oil, which can be stored and/or undergo further processing. Crude oil can be refined to produce a final oil product. Methods for refining crude oil to obtain a final oil are known to those of ordinary skill in the art. Hui (1996) provides a thorough review of oils and oilseeds (Bailey's Industrial Oil and Fat Products, Fifth Ed., Vol. 2, Wiley and Sons, Inc., New York, 1996). Chapter three of Hui (pp. 125–158), the disclosure of which is hereby incorporated by reference, specifically describes corn oil composition and processing methods. Crude oil isolated using the flaking methods described herein is of a high quality but can be further purified as needed using conventional oil refining methods.

In a preferred embodiment, the present invention relates to a method of recovering lighter particles, such as fines, during the processing of high oil corn. As used herein, the term "fines" means any particle of the corn process that passes through a #18 sieve having a 1.00 mm opening as defined in ASTM E-11 specifications. The recovery of the particles may occur before, after, or during any step in the process, such as during the moisture removal step, during the cracking step or before or after the flaking process. In general, fines are recovered by passing a current of gas (e.g., air, nitrogen, argon) over the corn at a suitable velocity and direction such that smaller and lighter particles are carried away in the stream, leaving behind larger and heavier particles. Alternatively, lighter particles can be separated from heavier particles using a liquid spray (e.g., water, process water). The liquid is applied broadly enough so as to physically eliminate the lighter, airborne particles. The liquid spray can include components that add value to the end product, such as vitamins, minerals, enzymes, and combinations thereof. In addition, the liquid spray can further comprise a caustic liquid. Regardless of the separation method, these fine particles can be captured or recovered by any method known in the art such as using a baghouse. Preferably, the recovered lighter particles can be reintroduced into starch-containing product streams for the recovery of starch. Additionally the fines may be sold as an animal feed.

Corn endosperm includes some valuable components such as carotenoids, lutein, and zeaxanthin. Carotenoids in grains are classified into two general groups, the carotenes and the xanthophylls. The carotenes are important because they are vitamin A precursors. Blessin et al. (*Cereal Chemistry*, 40, 582–586 (1963)) found that over 90% of the carotenoids, of which beta-carotene is predominant, are located in the endosperm of yellow dent corn and less than 5% are located in the germ. Vitamin A is derived primarily from beta-carotene.

Another group of valuable components found in the endosperm includes the tocotrienols. Grams et al. (1970) discovered that in corn, tocotrienols were found only in the endosperm, whereas the germ contained most of the tocopherols. Tocotrienols can be extracted from plant material using various solvents. Processes for recovering tocotrienols from plant material are described by Lane et al. in U.S. Pat. No. 5,908,940, the entire disclosure of which is incorporated by reference.

Accordingly, the process described herein provides a nutritionally enhanced corn oil enriched with lutein, zeaxanthin, and/or beta-carotene and optionally one or more other nutritional components.

Oil-based products made with corn oil obtained by the extraction method described herein can contain higher levels of important nutrients than similar products made with corn oil produced by conventional methods. The corn oil obtained by the extraction methods described herein will include the corn oil from the germ and endosperm, and one or more other components extracted from the rest of the kernel. The one or more other components can be oil from the endosperm, tocotrienols, tocopherols, carotenoids, carotenes, xanthophylls, and sterols.

Tocopherols (vitamin E) and vitamin A are antioxidants and fat-soluble vitamins. When included in the diet, both have demonstrated health benefits. Blending of oil of the present invention with other oils or substances to achieve an appropriate level of beta-carotene, vitamin E, and tocotrienols is deemed within the scope of the present invention. In some embodiments, extracted corn oil prepared as described herein comprises about 0.1 percent by weight to about 0.5 percent by weight of tocopherol.

Oil produced in accordance with the present invention also may include approximately a 200% to 300% increase in tocotrienol content over conventionally-produced crude corn oil. Using the method of optionally tempering, cracking and/or conditioning and/or flaking and extraction of high oil corn, the corn oil was extracted and was then analyzed for tocotrienol content. The actual minimum and maximum values for tocotrienol content will depend upon the particular high oil corn used.

The oxidative stability index (OSI), measured in hours, is a measure of an oil's relative stability toward oxidation. Generally, the greater the OSI, the less susceptible the oil is toward oxidation and the longer it takes to oxidize the oil under test or use conditions. In addition, the greater the content of unsaturated fatty acids present in the oil, the lower the OSI. Exemplary oils prepared according to the extraction method described herein generally possess OSI values ranging from about 10–22 h.

Extraction of carotenes and xanthophylls and other pigments is described in detail by Blessin (*Cereal Chemistry*, 39, 236–242 (1962); the entire disclosure of which is incorporated by reference). Combinations of solvents, primarily ethanol and hexanes, can be used to extract carotenes and xanthophylls from corn. Ethanol, hexanes, other solvents combinations, and ratios thereof may be used to produce oil of the present invention on a commercial scale.

Exemplary embodiments of the crude oil obtained according to the extraction method described herein generally possess the partial composition profile featured in Table 4.

TABLE 4

| Component | Exemplary Extracted High Oil Corn | Extracted High Oil Corn (Range) |
| --- | --- | --- |
| FFA (%) | 1.45 | 0.7–3.00 |
| C16:0 | 11.4 | 10–14 |
| C18:0 | 2.1 | 1.5–3.5 |
| C18:1, cis | 33 | 26–50 |
| C18:1, trans | — | — |
| C18:2, cis | 50 | 42–60 |
| C18:2, trans | — | — |
| C18:3 | 0.8 | 0.6–1.6 |
| Phosphorus (ppm) | 190 | 100–400 |
| Total Tocopherols (ppm) | 0.13 | 0.1–.50 |

Fatty acids generally found in the corn oil generally include palmitic, stearic, oleic, linoleic and linolenic acids.

The crude oil prepared according to the methods described herein can be subsequently partially or completely hydrogenated. Suitable methods for partially or completely hydrogenating oil are described in D. R. Erickson, Practical Handbook of Soybean Processing Utilization (1995, AOCS Press), the entire disclosure of which is hereby incorporated by reference.

When making oil-based products according to the invention, those products can include conventional corn oil, soy oil, canola oil, olive oil, palm oil, sunflower oil, safflower oil, antioxidant, flavoring, hydrogenated oil, partially hydrogenated oil and/or animal fat. By mixing the corn oil herein with one or more other oils, blended oil products are made. The corn oil-based products can also include materials such as food additives, salt, fat, food colors, β-carotene, annatto extract, curcumin or tumeric, β-apo-8'-carotenal and methyl and ethyl esters thereof, natural or synthetic flavors, antioxidants, propyl gallate, butylated hydroxytoluene, butylated hydroxyanisole, natural or synthetic tocopherols, ascorbyl palmitate, ascorbyl stearate, dilauryl thiodiproprionate, antioxidant synergists, citric acid, sodium citrate, isopropyl citrate, phosphoric acid, monoglyceride citrate, anti-foaming agent, dimethyl polysiloxane, crystallization inhibitor, oxystearin, amino acids, vitamin, minerals, carbohydrates, sugars, herbs, spices, acidity regulators, firming agents, enzyme preparations, flour treatment agents, viscosity control agents, enzymes, lipids, and/or vegetable or animal protein. Additionally, these edible products can be enhanced or enriched with protein supplements containing utilizable protein. An exemplary food product such as a breakfast cereal could include ingredients such as meal of the invention, wheat and oat flour, sugar, salt, corn syrup, milled corn, dried fruit, vitamin C, B vitamins, folic acid, baking soda, and flavorings.

Other exemplary oil-based products that can comprise the oil prepared herein include food oil, cooking oil, edible oil and blended oil.

Equipment used for the extraction of oil from oilseeds, such as soybean and canola, can be used to prepare the corn oil and extracted corn meal described herein. Useful commercial-scale oilseed flakers can be obtained from French Oil Mill Machinery Company, Piqua, Ohio; Roskamp Champion, Waterloo, Iowa; Buhler, based in Switzerland with offices in Plymouth, Minn.; Bauermeister, Inc., Germany; Consolidated Process Machinery Roskamp Company, on the world wide web at http://www.cpmroskamp.com, and Crown Iron Works, Minneapolis, Minn.

Commercial-scale methods and equipment are sufficient for extracting corn oil from at least about 1 ton of corn per day. In some embodiments, the capacity of commercial-scale operations ranges from about 100 tons of corn per day to about 3000 tons of corn per day, or the capacity ranges from about 700 tons of corn per day to about 1700 tons of corn per day. Commercial-scale operations that process greater than about 3000 tons of corn per day are also sufficient.

Corn oil or corn meal quality is determined by evaluating one or more quality parameters such as the oil yield, phosphorus content, free fatty acid percentage, the neutral starch percentage, protein content, and moisture content. Any method can be used to calculate one or more of the quality parameters for evaluating the oil or meal quality.

The phosphorus concentration of crude oil can be determined using AOCS method Ca 12-55. AOCS method Ca 12-55 identifies the phosphorus or the equivalent phosphatide zinc oxide, followed by the spectrophotometric measurement of phosphorus as a blue phosphomolybdic acid complex. AOCS method Ca 12-55 is applicable to crude, degummed, and refined vegetable oils. The phosphorus concentration is converted to phospholipid concentration, i.e., gum concentration, by multiplying the phosphorus concentration by 30. In some embodiments, corn oil produced according to the invention includes about 100–400 parts per million (ppm) of phosphorus.

The free fatty acid percentage of oil can be determined using AOCS method Ca 5a-40. AOCS method Ca 5a-40 identifies the free fatty acids existing in the oils sample. AOCS method Ca 5a-40 is applicable to all crude and refined vegetable oils, marine oils, and animal fats. The neutral oil loss during processing is determined by adding the gum percentage and the free fatty acid percentage together. The amount of free fatty acid obtained in the extracted corn oil will depend upon the amount of fatty acids found within the high oil corn from which the oil was extracted. In some embodiments, the free fatty acid content of the extracted oil ranges from about 0.70 percent by weight to 3.00 percent by weight Oil color can be determined using AOCS method Cc 13b-45. AOCS method Cc 13b-45 identifies the color of an oil sample by comparing the oil sample with known color characteristics. AOCS method Cc 13b-45 is applicable to fats and oils provided no turbidity is present in the sample. Color values are evaluated qualitatively by visual inspection of the oil. Generally, visual inspection results in an oil being classified as a light oil or a dark oil compared to a known oil color. Color values are quantitated by determining a red color value and a yellow color value using the AOCS method Cc 13b-45. Typically, crude corn oil isolated using conventional dry milling methods has a red color value ranging from about 7 to about 10 and a yellow color value ranging from about 60 to about 70. Corn oils isolated using flaking methods described herein have oil colors that qualitatively are considered light and generally are lighter than crude corn oil derived from wet or dry milling techniques. The yellow color values may range from about 60 to about 70 and red color values may range from about 7 to about 10, as determined by AOCS Method Cc 13b-45.

The extracted corn oil can be used as a raw material for chemical modification, a component of biodegradable plastic, a component of a blended food product, a component of an edible oil or cooking oil, lubricant or a component thereof, biodiesel or a component thereof, a component of a snack food, a fermentation process raw material, and a component of cosmetics. Since the oil obtained by the extraction process herein has one or more components obtained from non-germ parts of the corn kernel, the oil is enhanced. In some embodiments, the oil will have an oleic range from about 20% to 80%, or preferably 25% to 50%, whereas normal corn has about 25% to 40% oleic acid in the oil. When making blended oils with the extracted oil, the blending can be done before, during or after the extraction process.

Biodiesel can be produced using the extracted corn oil of the invention. Biodiesel is a general term used for a variety of ester-based oxygenated fuels. Biodiesel produced today is a mixture of fatty acid methyl esters produced by methylating refined vegetable oil. Refined oil is preferable to crude oil or spent fryer oil due primarily to the quality of the glycerol by-product. The main drawbacks with previous biodiesel products and related vegetable oil lubricants are low temperature properties and reactivity toward oxidation and polymerization. A preferred biodiesel product comprises a low cloud point, reduced stearic and polyunsaturated fatty acid content, and high oleic acid content. Pour point correlates with low temperature properties and is influenced by the saturated fatty acid content of the oil. Polyunsaturated fatty acids are more susceptible to oxidation and polymerization reactions.

Solvent-extracted corn (SEC) oil exhibits improved cloud point performance over soy, while exhibiting similar chemical stability.

TABLE 5

| Oil | % Palmitic (16:0) | % Stearic (18:0) | % Oleic (18:1) | % Linoleic (18:2) | % Linolenic (18:3) | % Erucic (22:1) |
|---|---|---|---|---|---|---|
| Rape | 3 | 1 | 14 | 12 | 7 | 49 |
| Canola | 4 | 1 | 60 | 20 | 9 | 2 |
| Soy | 8–10 | 4 | 19–28 | 53–56 | 6–10 | 0 |
| SEC | 11 | 2 | 27 | 56 | — | — |

SEC oil corn can be further processed to form lubricants such as by published procedures practiced currently in the industry (see, e.g., U.S. Pat. No. 6,174,501).

Meal produced from the flaking and oil extraction process described herein is useful to produce unique feed products as well as serving as a feedstock for further processing steps. The corn meal used herein has been obtained after extraction of oil from whole kernels of high oil corn, wherein the kernel has not been separated into its constituent part, although the kernel may or may not have been ground, flaked, cracked, chipped, or abraded. The process of removing the oil from corn via extraction serves to concentrate the remaining nutrients such as protein and essential amino acids.

The extracted corn meal can be provided as a loose product or a pelleted product, optionally in combination with other components. For example, a pelleted product could include the extracted corn meal (by itself or in combination with other components) that has been pelleted and subsequently coated with zein protein. The corn meal can be included in blended meal products which can be provided in loose or pelleted form. The corn meal of the invention will generally comprise the components in the approximate amounts indicated in Table 6 below.

TABLE 6

| Component | Sample A Amount (%) | Sample B Amount (%) | Sample C Amount (%) |
|---|---|---|---|
| Moisture | 5–45 | 5–25 | 5–45 |
| Starch | 40–70 | 40–80 | 40–70 |
| Protein | 8–20 | 7–20 | 8–20 |
| Fat (Oil) | 0.75–6 | 0.75–6.0 | 0.75–12 |
| Crude Fiber | 2–4 | 2–4 | — |
| Ash | 1.5–3 | 0.5–2.0 | — |
| Fructose | 0.15–0.3 | — | — |
| Glucose | 0.2–0.5 | — | — |
| Sucrose | 1.5–2.5 | — | — |
| Lysine | — | — | 0.2–2.0 |
| Tryptophan | — | — | 0.03–2.0 |

The corn meals above may also further comprise unspecified amounts of the components for which no amounts have been indicated.

Meal mixtures may be made by mixing various materials such as grains, seed meals, vitamins, and/or purified amino acids together to form a composite material that meets specific dietary requirements for protein, fat, vitamins, minerals, and other nutrients. The mixing process can include grinding and blending the components to produce a relatively homogeneous mixture of nutrients. Physical properties of the feed raw materials and of the compounded feed affect the quality, storability, and overall value of the products.

The extracted corn meal may be somewhat analogous to steam-flaked corn. As discussed herein, specific oil levels can be achieved in the extracted meal by altering processing conditions. The protein, amino acid, and oil levels of the present extracted meal cannot be achieved in steam-flaked normal corn, and steam-flaked high oil corn may yield a meal having excessive oil content.

Solvent extracted corn meal is useful for fermentation-based production of compounds, such as, for example, ethanol, citric acid, lactic acid, and vitamins. Solvent extracted corn meal from fermented high oil corn can be hydrolyzed to provide soluble sugars. The meal serves as a carbon and nitrogen source for bacterial, fingal, or yeast cultures. Biotin and other vitamins can be produced through the cultivation of microorganisms. Organisms can include *Pseudomonas mutabilis* (ATCC 31014), *Corynebacterium primorioxydans* (ATCC 31015), Arthrobacter species, Gibberella species, Penicillium species, or combinations thereof.

Nutrients used in the cultivation of these and other microorganisms include, for example, starch, glucose, alcohols, ketones, and as a nitrogen source, peptone, corn steep liquor, soybean powder, ammonium chloride, ammonium sulfate, ammonium nitrate, extracted corn meal, or urea. Various salts and trace elements may also be included in media for the culture of microorganisms. The pH of the culture medium is about 4 to about 9, preferably about 6 to about 8 and most preferably about 7 for bacterial species. The pH is about 5 to about 7 for mold or yeast. During cultivation, temperatures are kept between 10° C. to 100° C., preferably between 20° C. to 80° C., more preferably between about 20° C. to 40° C., and most preferably about 25° C.

Biotin production is described in U.S. Pat. No. 3,859,167, incorporated herein by reference. Cis-tetrahydro-2-oxo-4-n-pentyl-thieno[3,4-d]imidazoline is added to a culture medium containing solvent extracted corn meal and other appropriate identified ingredients in combination with a microbial species capable of forming biotin. In general, the microorganism is cultivated for 1 to 10 days, preferably 1 to 8 days, and more preferably 2 to 7 days, after which time biotin is separated and purified. In one embodiment, to purify biotin, cells are removed from the culture medium, the filtrate is absorbed on activated charcoal, and purified with an ion exchange column. Alternative methods of purification are also used such as crystallization by adjusting the pH of the biotin-contained solution to near its isoelectric point.

Blended feedstocks comprising the extracted corn meal and one or more other oilseed meals or yellow dent corn meal may also be made by one or more of the following ways: 1) combining the high oil corn and the other seed prior to cracking and/or flaking and subjecting the entire seed mixture to the flaking and extraction process described herein to form a blended meal; 2) combining the high oil corn and the other seed after cracking and conditioning, but prior to flaking and subjecting the entire seed mixture to an extraction process as described herein to form a blended meal; 3) combining the high oil corn and the other seed after flaking and subjecting the entire seed mixture to the extraction process described herein to form a blended meal; 4) combining the extracted corn meal with extracted or non-extracted other seed meal to form a blended meal; or 5) combinations thereof to form a blended meal. At any time during these processes, additional components can be added to the blended meals to form a blended product. A blended feedstock may be desired for certain fermentation processes.

The extracted corn meal is useful as a raw material for production of corn protein isolates, for fermentation or for further chemical processing. In addition enzymes, such as amylases and proteases, can be added to the meal to help facilitate the breakdown of starch and proteins.

Several important quality parameters for the extracted meal include the fat, starch, protein, and moisture content. Methods for evaluating quality parameters of oilseed meals are disclosed in the AOCS methods, the relevant disclosure of which is hereby incorporated by reference. These methods can also be applied to the extracted corn meal prepared as described herein.

The moisture content of the grain can affect the flaking process. It may be necessary for the moisture of the corn grain to be increased by about 1% to about 15% before flaking the seed. Optimizing the grain moisture content to facilitate efficient processing is within the knowledge of those of ordinary skill in the art.

Corn meals derived using different methods or isolated at different times are compared by normalizing the meals to a common moisture content. The moisture content of an oilseed protein concentrate, such as a corn meal or whole corn, is determined using AOCS method Ba 2b-82. The crude fiber content of corn meal is determined using AOCS method Ba 6-84. AOCS method Ba 6-84 is useful for grains, meals, flours, feeds and all fiber bearing material from which the fat can be extracted leaving a workable residue. Crude protein content of corn meal is determined using AOCS method Ba 4e-93. The starch content of corn meal is determined using AOCS method Ba 4e-93. The starch content of corn meal is determined using the Standard Analytical Methods of the Member Companies of the Corn Refiners Association Incorporated, 2d Edition, Apr. 15, 1986, method A-20 ("Corn Refiner's method A-20").

It is to be understood that the analytical methods provided herein are illustrative examples of useful methods for computing various quality parameters for the oils and meals described herein. Other suitable methods are known and may be used to compute the quality parameters disclosed and claimed herein.

The following examples are included to demonstrate specific embodiments of the invention. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Processing High Oil Corn Using Cracking, Conditioning and Flaking Method

This example describes the process of obtaining corn oil and corn meal from high oil corn (about 12% oil). A 45-pound sample of high oil corn was cracked using a Roskamp 6.5 Series (9" two sets) set at a roll gap of 0.27 inches. A sample was taken for analysis and the remaining sample split into 4 sub-samples. Each of the four sub-samples was then conditioned independently to different temperatures (49° C. (120° F.), 65° C. (150° F.), 82° C. (180° F.), 93° C. (200° F.)). The samples were heated in a Crown™ 18 inch De-solventiser/Toaster. After each sample reached its conditioning temperature, the samples were passed through flaking rolls. The flaking rolls used were a Ross 10-inch set to a gap of 0.007 inches. A sample of the flakes was taken and about a 500 gram sample was extracted. The flaked sample was washed for four 20-minute periods with 1200 ml of hexanes each period for a total of 4800 ml of solvent over 80 min. The solvent temperature was about 49° C. (120° F.). The miscella was collected and filtered through #4 qualitative circles each having a diameter of 185 mm. The filtered miscella was roto-evaporated to estimate the percent oil recovery. The meal was air dried at room temperature. Samples of the oil and meal were taken and analyzed for fatty acid profile, starch, protein and fiber. During the extraction a sieve analysis was performed and flake thickness was measured.

Other equipment used for the analysis included a Mettler Toledo™ HR73 Halogen Moisture Analyzer, Ohaus Explore™ scale, Büchi R-114 Roto-Vap™, Crown™ extractor screen 0.032 sieve and a easy-load master Flex Model 7529-30 pump.

The color of the crude oil was visually evaluated and determined to be a light yellow color compared to crude oil isolated using conventional wet milling methods, which was a dark brown color.

The desolventized corn meal was characterized using AOCS methods Ba 3-38, Ba 2b-82, Ba 6-84, and Ba 4e-93, and Corn Refiner's Method A-20. When normalized to 10% moisture content, the corn meal had about 3.2% fiber content, about 65% starch content, and about 14% protein content. Meal fat was determined to be about 1.07% using AOCS method Ba 3-38. For comparison, corn gluten feed created using conventional wet milling methods and normalized to a 10% moisture content can be expected to contain an oil content of about 4%, a protein content of about 20%, and a fiber and other carbohydrate content of about 60%. Also for comparison, corn gluten meal created using conventional wet milling methods and normalized to a 10% moisture content can be expected to contain an oil content of about 3%, a protein content of about 60%, and a fiber and other carbohydrate content of about 22%.

The nutrient profiles of two types of meal (1.5 percent by weight oil and 4.0 percent by weight oil) produced according to this process are shown in Table 7. Amounts are expressed on an "as is" or "as fed" moisture level.

TABLE 7

| Component | Meal Sample 1 Amount (%) | Meal Sample 2 Amount (%) |
| --- | --- | --- |
| Moisture | 12 | 12 |
| Oil | 1.5 | 4 |
| Protein | 10.5 | 10.2 |
| Starch | 58.0 | 56.3 |
| Neutral Detergent Fiber | 11.3 | 11 |
| Acid Detergent Fiber | 2.8 | 2.8 |
| Ash | 1.4 | 1.3 |
| Lysine | 0.39 | 0.37 |
| Tryptophan | 0.105 | 0.102 |
| Methionine | 0.29 | 0.28 |
| Cystine | 0.25 | 0.24 |
| Total Sulfur Amino Acids | 0.54 | 0.52 |
| Valine | 0.53 | 0.51 |
| Isoleucine | 0.40 | 0.39 |
| Arginine | 0.53 | 0.51 |
| Threonine | 0.40 | 0.39 |
| Leucine | 1.20 | 1.17 |
| Histidine | 0.32 | 0.31 |
| Phenylalanine | 0.51 | 0.5 |
| Alanine | 0.82 | 0.79 |
| Serine | 0.54 | 0.52 |
| True metabolizable energy (TMEn; kcal/kg) | 3023 | 3133 |

TABLE 7-continued

| Component | Meal Sample 1 Amount (%) | Meal Sample 2 Amount (%) |
|---|---|---|
| Swine metabolizable energy (ME; kcal/kg) | 3191 | 3301 |

When compared to meals made from conventional corn, the extracted corn meal described herein provides a greater amount of key nutritional components such as vitamins, folic acid, pantothenic acid, lysine, tryptophan, and/or niacin. For example, Meal Samples 1 and 2 of extracted corn meal that are prepared above include the nutritional components in the amounts shown in Table 8. Amounts for the same components, to the extent they are found in yellow corn that has not been processed as described herein, are included for comparison.

TABLE 8

| Component | Yellow Corn | Meal Sample 1 | Meal Sample 2 |
|---|---|---|---|
| Vitamin B6 (mg/100 g) | 0.400 | 0.820 | 0.660 |
| Vitamin B12 (mg/100 g) | 0.500 | 0.500 | 0.500 |
| Folic Acid (µg/100 g) | — | 25.0 | 25.0 |
| Pantothenic Acid (mg/100 g) | — | 0.660 | 0.890 |
| Niacin (mg/100 g) | 2.05 | 2.30 | 1.15 |

The extracted corn meal prepared as described herein advantageously can be made to contain specific levels of oil and, in particular, specific ratios of oil to protein, of oil to carbohydrate or of oil to protein to carbohydrate. For example, normal corn with 8 percent by weight protein and 4 percent by weight oil has a protein:oil ratio of 2.0, and high oil corn with 9 percent by weight protein and 12 percent by weight oil has a protein:oil ratio of 0.75. Meal produced by extraction to have 10.5 percent by weight protein and 1.5 percent by weight oil has a protein:oil ratio of 7.0. This higher ratio makes this meal type and products made from it desirable for certain applications, one example being a swine-finishing ration.

The present invention provides an extracted corn oil with greater amounts of lutein, zeaxanthin and beta-carotene than commercially available crude oil obtained from commodity normal yellow dent corn. Conventional crude oil can be obtained from suppliers such as Cargill, Incorporated (Minneapolis, Minn.). For example, a corn oil prepared as described above comprised the ingredients shown in Table 9 in the amounts indicated as compared to commercially available crude oil.

TABLE 9

| Sample | Lutein (mg/g) | Zeaxanthin (mg/g) | Beta-Carotene (IU/100 g) |
|---|---|---|---|
| Commercial Crude Corn Oil | 0.005 | 0.005 | 15.5 |
| Oil Sample 1 | 0.04 | 0.012 | 72.3 |
| Oil Sample 2 | 0.330 | 0.112 | 302 |

EXAMPLE 2

Process of Obtaining Oil From High Oil Corn With Increased Tocotrienol Content

In this example, oil with approximately a 200% to 300% increase in tocotrienol content over conventionally produced crude corn oil is described. Using the method of flaking and extraction of Example 1, corn oil was extracted from high oil corn grain having an oil content of about 12 percent by weight. The corn oil was then analyzed for tocotrienol content. The table below includes data concerning the alpha- and gamma-tocotrienol content of conventional corn oils produced by conventional processing of conventional corn and the extracted corn oil prepared according to the method of Example 1. Conventional Crude oil refers to an unrefined corn oil sample. The sample is representative of corn oil of the type that is most commonly produced presently. As noted below, the tocotrienol content of extracted whole kernel oil (EWKO) samples from two different high oil corn samples that were extracted with solvent at temperatures ranging from 49 to 93° C. (120 to 200° F.) was found to be approximately two to three times higher than in the conventional crude oil sample. As shown in Table 10, the tocotrienol content of the EWKO samples ranged from about 26 parts per million (ppm) to about 33 ppm of α-tocotrienol and from about 48 ppm to about 84 ppm of γ-tocotrienol. Generally, increasing the extraction temperature results in an increase in the tocotrienol content of the extracted corn oil. The actual minimum and maximum values for tocotrienol content will depend upon the particular high oil corn used.

TABLE 10

| Sample | α-tocotrienol (ppm) | γ-tocotrienol (ppm) |
|---|---|---|
| Conventional Crude Oil (Control) | 11.88 | 29.94 |
| EWKO 1 (49–93° C.) | 29.36–33.19 | 48.11–59.36 |
| EWKO 2 (49° C.) | 26.05–28.43 | 79.55–84.21 |

Accordingly, the process of Example 1 is used to make an extracted corn oil comprising elevated levels of tocotrienols.

EXAMPLE 3

Use of Meal Derived From Corn Processed Through Flaking and Extraction as a Component of a Blended Animal Feed Product Comprised of Corn Meal and a Second Meal This example illustrates a novel feed ingredient comprised of a blend of a corn meal produced by the flaking and oil extraction method and another plant-based meal such as an oilseed meal. This blended material could be in the form of simply a loose aggregate mixture of both meal types or a pelleted product. Because the method for producing the corn and oilseed meals would be similar, i.e., cracking, conditioning, flaking and solvent extraction, it is possible to produce both meals in proximity and blend them prior to shipment to a customer. An advantage of this approach is that varying protein and energy levels can be created in a single meal. Additional ingredients are optionally added either at the meal blending stage or later. For example, an energy-intensive step in feed manufacturing involves grinding corn grain and blending it with other ingredients at a feed mill. The present blended meal generally requires less energy to produce a finished feed product than does a conventional blended meal.

Table 11 shows nutrient profiles of soybean meal (SBM), extracted corn meal (ECM), a blend of 20% SBM and 80% ECM (S20-C80), a blend of 10% SBM and 90% ECM (S10-C90). The ECM was prepared according to Example 1.

TABLE 11

| Parameter | SBM | ECM | 20% SBM & 80% ECM | 10% SBM & 90% ECM |
|---|---|---|---|---|
| Crude Protein (CP) | 47.5 | 10.2 | 17.66 | 13.93 |
| Swine ME, kcal/kg | 3380 | 3301 | 3316.8 | 3308.90 |
| Poultry ME, kcal/kg | 2440 | 3133 | 2994.4 | 3063.70 |
| Crude Fat, % | 3 | 4 | 3.8 | 3.90 |
| Neutral Detergent Fiber, % | 8.9 | 11.3 | 10.82 | 11.06 |
| Acid Detergent Fiber, % | 5.4 | 2.8 | 3.32 | 3.06 |
| Arginine | 3.48 | 0.45 | 1.06 | 0.75 |
| Histidine | 1.28 | 0.27 | 0.47 | 0.37 |
| Isoleucine | 2.16 | 0.34 | 0.70 | 0.52 |
| Leucine | 3.66 | 1.03 | 1.56 | 1.29 |
| Lysine | 3.02 | 0.33 | 0.87 | 0.60 |
| Methionine | 0.67 | 0.25 | 0.33 | 0.29 |
| Cysteine | 0.74 | 0.21 | 0.32 | 0.26 |
| Phenylalanine | 2.39 | 0.44 | 0.83 | 0.64 |
| Tyrosine | 1.82 | 0.29 | 0.60 | 0.44 |
| Threonine | 1.85 | 0.34 | 0.64 | 0.49 |
| Tryptophan | 0.65 | 0.09 | 0.20 | 0.15 |
| Valine | 2.27 | 0.45 | 0.81 | 0.63 |
| Total Essential Amino Acids (EAA) | 23.99 | 4.49 | 8.39 | 6.44 |
| EAA/CP | 0.505 | 0.440 | 0.45 | 0.45 |

EXAMPLE 4

Processing High Oil Corn Using Flaking Method

Shelled kernels of individual ears of yellow dent corn were screened for a total oil content greater than about 7 percent by weight oil using a Perten™ bulk near infrared (NIR) seed tester (model 9100-H.F) Perten Instruments (Reno, Nev.). Kernels from the ears having at least a 7 percent by weight oil content were screened further for individual kernels having an oil content of at least 13 percent by weight oil in a Brimrose™ seedmeister single kernel NIR tester (Brimrose Corp., Baltimore, Md.). The kernels were stored at a moisture content of about 13.5%. At the time of processing, the moisture content of the seed was about 10%.

A bench scale flaking apparatus containing a two-inch stainless steel rod and plate was used to flake the whole corn grain. The whole corn grain sample was passed through the rollers four times to obtain a final flake thickness of about 0.01 inches. A miscella was extracted from the flaked corn grain using hot (60° C. to 65° C.) n-hexane and a Kimble™ model 585050 Soxhlet extractor. The resulting miscella and corn meal were desolventized. The miscella was desolventized by heating the miscella to 70EC under a vacuum of 25 inches of mercury. The corn meal was desolventized according to AOCS method Ba 2a-38.

The total recovered oil was determined to be 14.74 percent by weight of the whole corn grain sample. The phosphorus content of the desolventized crude oil was determined to be 365 ppm using AOCS method Ca 12-55. The phospholipid concentration was determined to be 1.095% (0.0365%*30). The free fatty acid content was determined to be 0.2% using AOCS method Ca 5a-40. The neutral oil loss during processing was determined to be 1.3% (1.095%+0.2%). Using the same methods, crude oil extracted from normal, i.e., 3–4 percent by weight total oil content, corn grain using conventional wet milling methods can be expected to have a phosphorus content from about 600 ppm to about 800 ppm, a free fatty acid concentration from about 0.5% to about 1% and a neutral oil loss during processing ranging from about 3% to about 4%.

The color of the crude oil was visually evaluated and determined to be a light yellow color compared to a crude oil isolated using conventional wet milling methods, which was a dark brown color.

The desolventized corn meal was characterized using AOCS methods Ba 3-38, Ba 2b-82, Ba 6-84, and Ba 4e-93, and Corn Refiner's Method A-20. When normalized to a 10% moisture content, the corn meal had a 3.2% fiber content, a 65% starch content, and a 14% protein content. Meal fat was determined to be 1.07% using AOCS method Ba 3-38. For comparison, corn gluten feed created using conventional wet milling methods and normalized to a 10% moisture content can be expected to contain an oil content of about 4%, a protein content of about 20%, and a fiber and other carbohydrate content of about 60%. Also for comparison, corn gluten meal created using conventional wet milling methods and normalized to a 10% moisture content can be expected to contain an oil content of about 3%, a protein content of about 60%, and a fiber and other carbohydrate content of about 22%.

EXAMPLE 5

Process of Refining High Oil Corn

This example describes a continuous solvent extraction process in the context of the present invention. The extraction process consisted fundamentally of four parts: pre-extraction, extraction, meal desolventization, and oil desolventization. These various stages are described in further detail below.

(A) Pre-extraction 5.4 tons of whole kernel high oil corn (approximately 12 percent by weight oil) was tempered and then gate fed from a porta-bin to a bucket elevator to a cracking mill. From the cracking mill, cracks (i.e., particles of whole corn) were conveyed to a conditioner, which discharged to an insulated conveyance system. This system consisted of a second bucket elevator, air mechanical conveyor, heated steam jacketed conveyor, and chutes connected in series. From the conveyance system, corn cracks were fed to a flaking roll.

Prior to transport to the cracking mill, whole corn was tempered to nominally 14.5% moisture by adding water to "as is" moisture corn in a 350 liter Toronto Coppersmithing™ Toreo Model R-12 ribbon blender. Water was sprayed into the vessel at a rate of 2 liters/h. After the appropriate amount of water was added, the corn was stirred for another hour. The corn was then allowed to soak for 24 h before being tested for moisture. The tempered corn was then stored for 11 days to 15 days.

After storage, the tempered corn was cracked at ambient temperature using a Roskamp™ (Waterloo, Iowa) model number 6.5 series double stand cracking roll having rolls with 9" diameters and 12" lengths. Both top and bottom rolls were set such that one roll rotated faster than the other. The fast rolls rotated at 1065 revolutions per minute (rpm) with 6 spiral RBV cut corrugations per inch. The slow rolls were cut identically but rotated at 708 rpm. Crack moistures were 13.3% to 15.7%. Cracks of the following average particle size distribution ranges were generated: 15.9% retained by US #4 mesh screens, 39.9% retained by US #6 mesh screens, 27.8% retained by US #8 mesh screens, 6.8% retained by US #10 mesh screens, 4.3% retained by US #18 mesh screens, and 5.3% passed through US #18 mesh screens.

The cracked corn was then conditioned in a two-deck nominal 100-kilogram capacity conditioner (Simon-Rosedowns, currently owned by De Smet; Prins Boudewijnlaan 265; B-2650 EDEGEM; Antwerp) with sweep arm agitation (36 inches in diameter, 20 inches high per deck). The bottom deck was run full. Residence time in the sparged steam section was 55 min. The top deck crack depth was varied to achieve a residence time in the indirect heating section averaging 39 min and for a total residence time was 94 min. Sparge steam addition was a rate from 0 to 5 kg/h. Conditioning exit moistures were in the range of 12.1% to 14.5%. Exit temperatures were in the range from 75° C. to 85° C.

Flakes were then generated from the cracked corn using a Roskamp (Waterloo, Iowa) model number 2862 flaking mill. The mill was 62 inch long and 28 inch wide rolls. The main drive was designed to turn the fast roll nominally at 300 rpm, and inter-roll drive (IRD) ratio was 8%. Roll pressure was held constant at 500 pounds per square inch gauge (psig). Flaking exit moistures were in the range of 9.1% to 11.7%. Exit temperatures were in the range from 60° C. to 83° C. Flake thickness ranged from 0.3 mm to 0.7 mm with the roll gap optimally set at 0.2 mm (0.008 inches).

(B) Extraction

A continuous 150 kg/h Crown™ (Roseville, Minn.) model 11 pilot extractor was used to process the flaked corn. This pilot scale extractor utilized mixed hexanes as a solvent with 5 counter-current miscella wash zones and a tail wash section. Six-miscella recirculation pumps were utilized with fresh hexanes at 50° C. to 60° C. fed in the upper portion of the extractor. The dimensions of the extractor were 29 feet long, 7.8 inches wide, and 4.5 inches deep. Twenty-three of the 29-foot extractor was wetted, of which 19.5 feet was subjected to washing. The average feed rate was approximately 75 kg/h. The residence time was approximately 60 min. The solvent-to-meal ratios were adjusted between 0.75:1 and 1.33:1. Full miscella was sent to the oil desolventization system at 27° C. to 34° C.

(C) Meal Desolventization

Ambient and indirect heat desolventization occurred first in a Schnecken™ (Crown Iron Works, Roseville, Minn.) steam jacketed conveyor (SJC). The SJC consisted of a hollow flight screw inside of a steam jacket (12 feet long, 10 inches in diameter). The open flight screw created a tumbling action as it conveyed the extracted material through the conveyor, thus ensuring that all material was exposed to the heated wall. A pneumatic controller regulated the amount of steam supplied to the jacket. The temperature at the outlet of the conveyor was monitored and used as the basis for the control of steam supplied to the jacket. Vapors from the conveyor were collected in the low vacuum condenser by the slight negative pressure developed by the system fan. A double-deck nominal 100 kg-capacity desolventizer and toaster (DT) with sweep arm agitation were utilized (36 inches in diameter, 20 inches high per deck). Steam sparge was piped through the top sweep arm only. Meal exit moistures ranged from 9.4% to 17.7%, and exit temperatures ranged from 57° C. to 104° C. Hexanes recovered from the SJC and extractor were condensed, dewatered, and recycled to the extractor.

(D) Oil Desolventization

Oil desolventization was executed using a rising film evaporator (RFE). This unit consisted of sixteen 1.5 cm diameter tubes inside a large jacket. The jacket was filled with steam, heating the tubes. The extract-laden liquid (normally oil in hexanes called miscella) was pumped into the bottom of the tubes. As it traveled up the inside of the tubes, steam heat caused the liquid to boil. The vapors held the liquid against the wall of the tube in a thin, rising film. At the top, the liquid and vapor were allowed to separate. The oil flowed into an overflow pipe to the oil stripper (OS), while the vapors were carried over to a condenser. The tubes were under vacuum so that the liquid boiled at a low temperature.

The oil stripper was a disc and donut style distillation column. The liquid was spread out in a thin film over a disc and dripped down onto a donut back onto a disc allowing the oil to cascade down the column. At the same time, steam was injected into the bottom of the stripper, which passed over the liquid film thereby removing the solvent remaining in the liquid. A steam jacket to keep the liquid and steam hot surrounded the disc and donut column. The oil stripper was also operated under vacuum. Hexanes recovered from the rising film evaporator and the OS were condensed, dewatered, and recycled to the extractor.

(E) Analysis of Oil Obtained From High Oil Corn

The oil was recovered and analyzed for vitamins, fatty acids, and micronutrients. As a control, 800 lbs. of yellow dent corn was extracted in an identical manner, and the recovered oil was analyzed for the same components. Vitamin A and β-carotene were analyzed by a contract lab using a proprietary procedure. Alternative published procedures include Bates, et al., *Proc. Fla. State Hort Soc.*, 88, 266–271 (1975). Free fatty acids were analyzed by gas chromatography (GC) using a CP88 cyanopropyl column (100 m×0.265 mm, 0.5 mm film thickness) and a flame ionization detector as described in American Oil Chemist Society (AOCS) methods Ce 1e-91, Ce2-66, Cd 3a-94 and Cd 1c-85.

Tocopherols and tocotrienols were analyzed by high performance liquid chromatography (HPLC, Waters model number 2590) using a normal phase silica column with hexane-isopropanol as the mobile phase and detected using fluorescence detection (Waters model number 2690), according to the procedure described in AOCS Ce 8–89. Lutein was analyzed by HPLC using a C30 reverse phase column with water-acetone mobile phase and detected with a UV detector.

Table 12, set forth below, presents a comparison of the oil composition obtained from high oil corn and yellow dent corn. For comparison, the composition of oil from yellow dent corn extracted in a corn wet milling process is also given.

TABLE 12

| Component | High Oil Corn | Yellow Dent Corn | Yellow Dent Corn, Wet Milling |
|---|---|---|---|
| Palmitic Acid % | 11.4 | 10.7 | 10.7 |
| Stearic Acid % | 2.2 | 1.9 | 2.0 |
| Oleic Acid % | 35.6 | 25.5 | 27.5 |
| Linoleic Acid % | 48 | 58.4 | 57.1 |
| Linolenic Acid % | 0.7 | 1.2 | 1.1 |
| α-Tocotrienol (ppm) | 184 | 48 | 12 |
| α-Tocopherol (ppm) | 237 | 231 | 136 |
| Vitamin B1, mg/100 g | 0.390 | NA | 0.260 |
| Vitamin B2, mg/100 g | 0.090 | NA | 0.080 |
| Vitamin B6, mg/100 g | 0.82 | NA | 0.4 |
| Vitamin B12, mg/100 g | 0.5 | NA | 0.5 |

EXAMPLE 6

Recovering Lighter Particles During Moisture Removal Step

This example sets forth one method of recovering lighter particles, such as fines, generated during the moisture removal step from the processing of high oil corn.

High oil corn is cracked and flaked as described in Example 5. The whole flaked corn from the flaking process is heated to remove moisture using standard processing equipment such as Kice SSI zig-zag classifier model A2612, (Kice Inc., Wichita, Kans.). During the moisture removal step, a controlled air stream is regulated such that the smaller and lighter particles are carried away, hence separating them from the heavier flakes. One such example of the controlled air stream is provided by a Crown™ multi-stage aspirating system operated at 2600 cubic feet per minute. The lighter particles are recovered by standard process equipment such as a baghouse. The recovered lighter particles are introduced into starch-containing product streams for the recovery of starch.

EXAMPLE 7

Method of Recovering Lighter Particles During Cracking Step With Air

This example sets forth one method of recovering lighter particles such as fines, generated during the cracking step from the processing of high oil corn.

Whole kernels from a high oil corn are cracked using a standard cracking mill roller such as Roskamp 6.5 Series, (Waterloo, Iowa). During this cracking step, a controlled air stream is directed to pass across the cracking mill roller, and the velocity of the air stream is regulated such that the smaller and lighter particles are carried away in the air stream, hence separating them from the heavier particles. One such example of the controlled air stream is provided by a Crown™ multi-stage aspirating system operated at 2600 cubic feet per minute. The lighter particles are recovered by standard process equipment such as a baghouse. The recovered lighter particles are introduced into starch-containing product streams for the recovery of starch.

EXAMPLE 8

Method of Recovering Lighter Particles With Liquid Spray

This example sets forth a method for the recovery of fines generated before and after the flaking process by means of a liquid spray.

High oil corn is processed as described in Example 7. The cracked corn prior to flaking and the corn flakes after the flaking process are sprayed or misted with a source of liquid providing broad enough coverage to physically eliminate the lighter, airborne particles. Water is used as the liquid. Alternatively, the liquid spray can be a substance that adds value to the resulting meal as well as recovers the value from the fines. The liquid spray is typically pure water, process water or water that has been supplemented with nutritional additives such as vitamins, enzymes or minerals. The liquid stream containing the particulates is carried away from the heavier particles in each case and is collected. The particulates are separated from the liquid using standard process equipment including a hydrocyclone or centrifuge. Optionally, the recovered fines may be dried before further use. The recovered lighter particles are then introduced into starch-containing product streams for the recovery of starch.

EXAMPLE 9

Production of Fermentation-Based Products (A) Starch Hydrolysis

Solvent extracted corn meal of the present invention prepared as described herein is a rich source of starch for fermentation. One method to provide soluble sugars suitable for fermentation is to hydrolyze starch molecules. Several types of enzymes that can be used to convert starch into simple sugars are amylase(s), proteases, cellulase(s) (e.g., xylonase), esterase(s) (e.g., ferulase, acetylesterase) and ligninase(s). These enzymes may be used alone or in combination.

Five samples (i.e., one sample of yellow dent corn grain (oil content 3.7% oil), two samples of high oil corn grain (Grain 1 8.7% oil, Grain 2 12.5% oil) and two samples of extracted high oil corn meal) (Meal 1 having 1.6% oil, Meal 2 having 1.9% oil) were ground to pass through a 1 mm screen using a Retsch Mill. High oil corn meal sample numbers 1 and 2, as shown in Table 16, were obtained from POS Pilot Plant Corporation (Saskatoon, Saskatchewan, Canada). Three hundred grams (300 g) of each sample was combined with 700 ml of water at 99° C.–100° C. comprising 0.5 ml α-amylase and placed in a sealed container. The pH of each mixture was adjusted to 5.9 with base. Each mixture was stirred for 45 min and additional α-amylase enzyme was added.

After an additional 45 min of incubation, the pH of each mixture was adjusted to 4.5 with acid. One-half of one milliliter (0.5 ml) glucoamylase (Optimax 7525) and 0.5 g protease (Fungal Protease 5000) were added to the sample mixtures and incubated with both enzymes at 62° C. for 22–24 h. Throughout the procedure, the degree of starch hydrolysis was monitored by HPLC (Waters 2690 Separations module) using an organic acid column (Aminex HPX-87H Ion Exclusion Column, 300 mm×7.8 mm, Bio Rad).

Total nitrogen content for each sample was determined by Leco 2000 CN. Free amino nitrogen (FAN) was determined by the AOAC method ($15^{th}$ Ed., 1990, p. 735). The amount of dextrose liberated from starch by the milling process and the amount of available nitrogen in the corn samples are set forth in Table 13.

TABLE 13

| Corn Sample | Calculated Initial Dextrose Content (g/L)♥ | Dextrose* (g/L) | Percent Starch Hydrolysis | FAN* (ppm) | Total Nitrogen (ppm)* | Oil Content (wt %) |
| --- | --- | --- | --- | --- | --- | --- |
| Yellow Dent Corn Grain | 251.94 | 175.6 | 69.70 | 223.8 | 2992 | 3.5 |
| High Oil Corn Grain 1 | 208.7 | 169.3 | 81.1 | 356.6 | 4288 | 12.8 |
| High Oil Corn Grain 2 | 208.8 | 150.6 | 72.1 | 339.0 | 4624 | 12.8 |
| High Oil Corn Meal 1 | 226.80 | 208.4 | 91.89 | 398.7 | 5920 | ~1.7 |
| High Oil Corn Meal 2 | 242.1 | 180.5 | 74.6 | 436.3 | 5296 | ~1.7 |

♥calculated based on starch content and a chemical gain of 1.11
*indicated "as is" values obtained from 30% starch hydrolysate.

Efficiency of starch hydrolysis varied among the different corn samples. High oil corn meal sample 1 exhibited 90% starch hydrolysis or better, the most efficient hydrolysis results. Yellow dent corn grain exhibited the least efficient starch hydrolysis, with a yield of 175.6 g/L dextrose obtained after hydrolysis of 251.94 g/L of dextrose.

High oil corn meal samples exhibited the highest average free amino nitrogen (FAN) and total nitrogen values. High oil corn grain samples displayed slightly less FAN and total nitrogen values, whereas yellow dent corn grain exhibited significantly lower results for free amino nitrogen and total nitrogen. As shown in Table 16, all high oil corn samples contain a higher amount of nitrogen than their yellow dent counterparts. Higher nitrogen levels may be due to higher initial protein in the high oil samples or higher susceptibility to protease treatment as compared to the yellow dent corn samples. As a whole, the milling procedure was consistent for all samples with weight losses due to evaporation maintained from 3%–5% by weight.

(B) Fermentation

Media for fermentations were normalized on a weight basis. Each sample comprised forty-five grams (45 g) of enzyme-treated and solvent extracted corn meal (resulting in starting dextrose concentrations of 133–233 g/L). Each sample was added to a 125 ml flask. Yeast extract was added at 1 g/L to ensure that nitrogen was not limiting. Cultures were inoculated with 10% inoculum from overnight yeast cultures (a typical Altech ethanol yeast of *Saccharomyces cerevisiae*) and incubations proceeded for 42 h at 30° C. on a rotary shaker at 125 rpm. Dextrose consumption and ethanol production were monitored by HPLC. Dextrose consumption and total ethanol productions by the yeast grown on dry-milled corn grain samples using equalized weight samples are shown in FIG. 1. Ethanol production by yeast grown on yellow dent corn grain samples was similar to productions by cultures grown on high oil corn grain samples 1 and 2.

Figure 2:
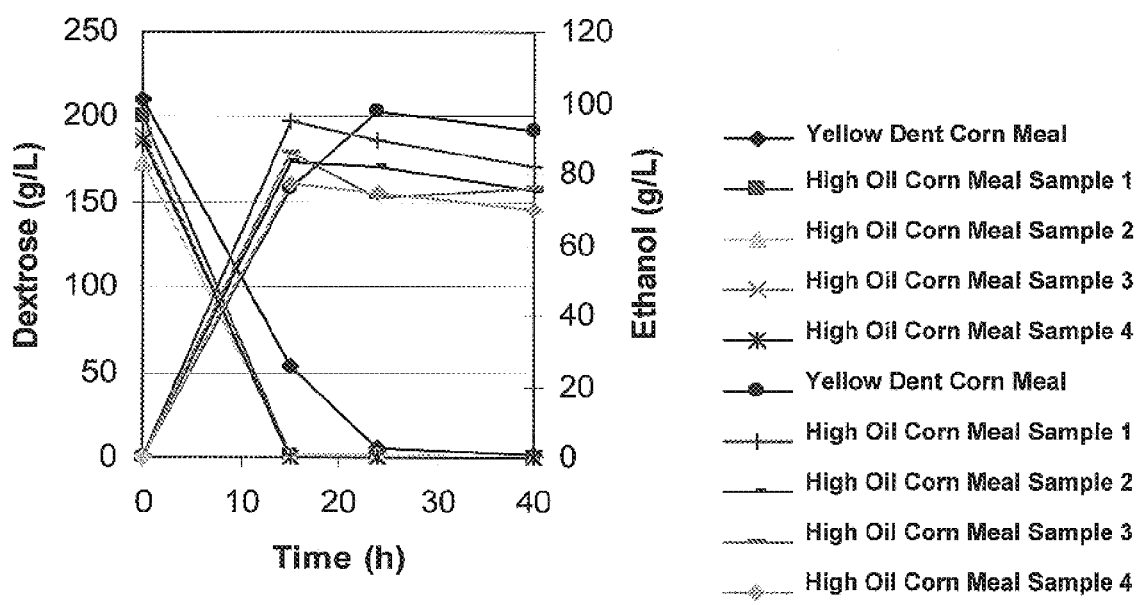
FIG. 2 illustrates the total amount of ethanol produced and dextrose consumed by yeast grown on oil-extracted yellow dent corn meal and high oil corn meal samples with equalized weight.

FIG. 2 displays the total ethanol production and dextrose consumption by yeast grown on oil-extracted corn meal samples with equalized weight.

Previous studies indicated that yeast grown on yellow dent corn with sugar concentrations near or above 25% did not provide maximal ethanol yields after 42 h. Consequently, media for fermentations were normalized on a weight basis, targeting an initial fermentable sugar concentration of approximately 180 g/L. Average starting dextrose concentrations for samples containing yellow dent corn grain, high oil corn grain and high oil corn meal are displayed in Table 14.

TABLE 14

| Corn Samples | Starting Dextrose Concentrations |
|---|---|
| Yellow Dent Corn Grain | 168.6 |
| High Oil Corn Grain 1 | 162.5 |
| High Oil Corn Grain 2 | 144.6 |
| High Oil Corn Meal 1 | 200.1 |
| High Oil Corn Meal 2 | 173.3 |

Cultures grown on high oil corn grain completely utilized the available dextrose, while the other cultures consumed dextrose to less than 1 g/L final concentration. Yellow dent corn grain and high oil corn meal samples displayed similar dextrose utilization curves. High oil corn grain and high oil corn meal samples reached over 75 g/L ethanol, but stopped production after 15 h as shown in FIGS. 1 and 2, possibly due to the limitation of a necessary nutrient.

Examination of ethanol productivity revealed that yeast grown on the high oil corn samples demonstrated the highest, producing over 5 g/L/h after 15 h, as displayed in Table 15. Productivity in these samples dropped after 15 h, however by this time all of the dextrose was exhausted.

TABLE 15

| | Ethanol Yield (g EtOH/g sugar) | | | Ethanol Productivity (g/L/h) | | |
|---|---|---|---|---|---|---|
| Fermentation media | 15 h | 24 h | 40 h | 15 h | 24 h | 40 h |
| Yellow Dent Corn Grain | 0.45 | 0.42 | 0.40 | 5.03 | 2.90 | 1.70 |
| High Oil Corn Grain 1 | 0.46 | 0.42 | 0.39 | 5.01 | 2.82 | 1.60 |
| High Oil Corn Grain 2 | 0.54 | 0.47 | 0.48 | 5.14 | 2.94 | 1.65 |
| High Oil Corn Meal 1 | 0.48 | 0.45 | 0.41 | 6.35 | 3.72 | 205 |
| High Oil Corn Meal 2 | 0.48 | 0.48 | 0.43 | 5.56 | 3.42 | 1.88 |

Weight Normalization

Figure 3:
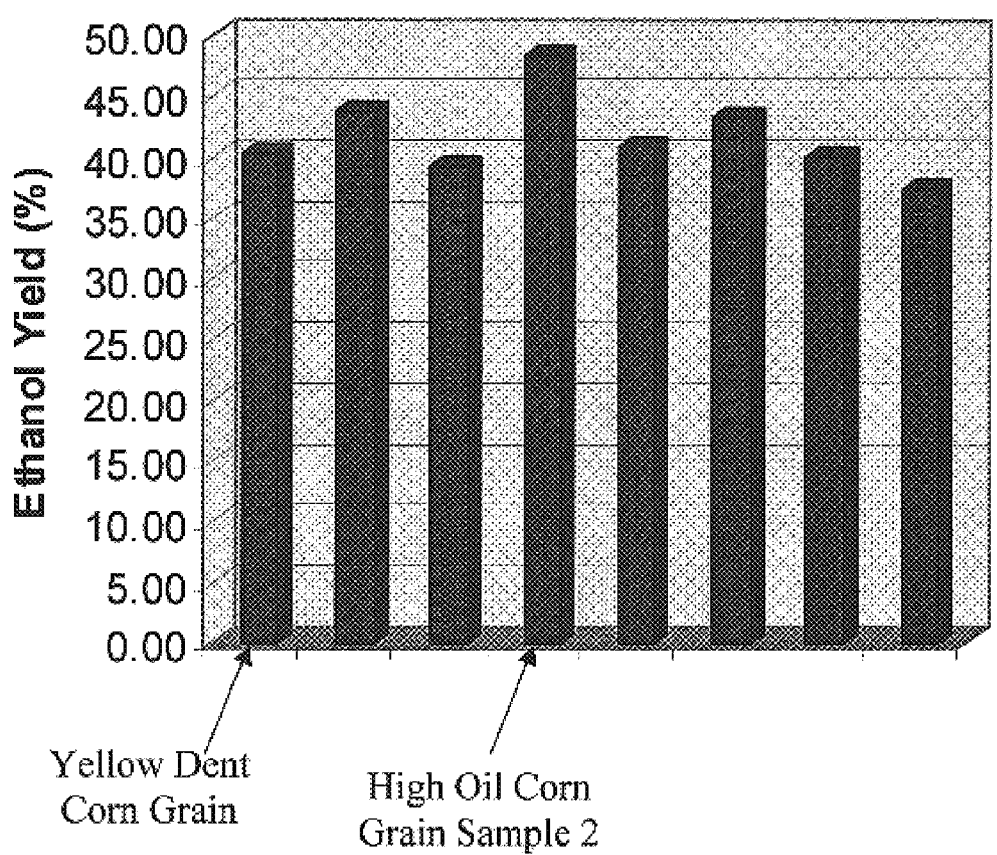
FIG. 3 displays the ethanol yields of yeast grown on corn samples.

Turning now to FIG. 3, ethanol yields at the end of the investigation were similar for most of the samples (i.e., most of the samples generated approximately 37–43% yield). High oil corn meal sample 2, however, was the exception and generated a 48% yield. The high ethanol yield in high oil corn meal sample 2 appears to exceed the theoretical amount allowed from the initial reported dextrose concentrations. Additionally, high oil corn meal sample 2 showed the least starting dextrose concentration as analyzed by HPLC. The high ethanol yield may be due to analytical error in the starting dextrose concentration.

Examination of ethanol productivity, as shown in Tables 15 and 16, revealed that most of the samples displayed around a productivity of 3 g/L/h. Two exceptions to this generalized result were for high oil corn meal samples 1 and 2. The results suggest that the lower oil content in these samples may support a faster ethanol production than samples containing a higher oil load. However, high oil corn meal sample 1 also had the highest starting dextrose concentration, which could also facilitate a faster ethanol production rate.

TABLE 16

| Fermentation media | Ethanol Productivity after 24 h |
|---|---|
| Yellow Dent Corn Grain | 2.90 |
| High Oil Corn Grain 1 | 2.82 |
| High Oil Corn Grain 2 | 2.94 |
| High Oil Corn Meal 1 | 3.72 |
| High Oil Corn Meal 2 | 3.42 |

Starch Normalization

Figure 4:
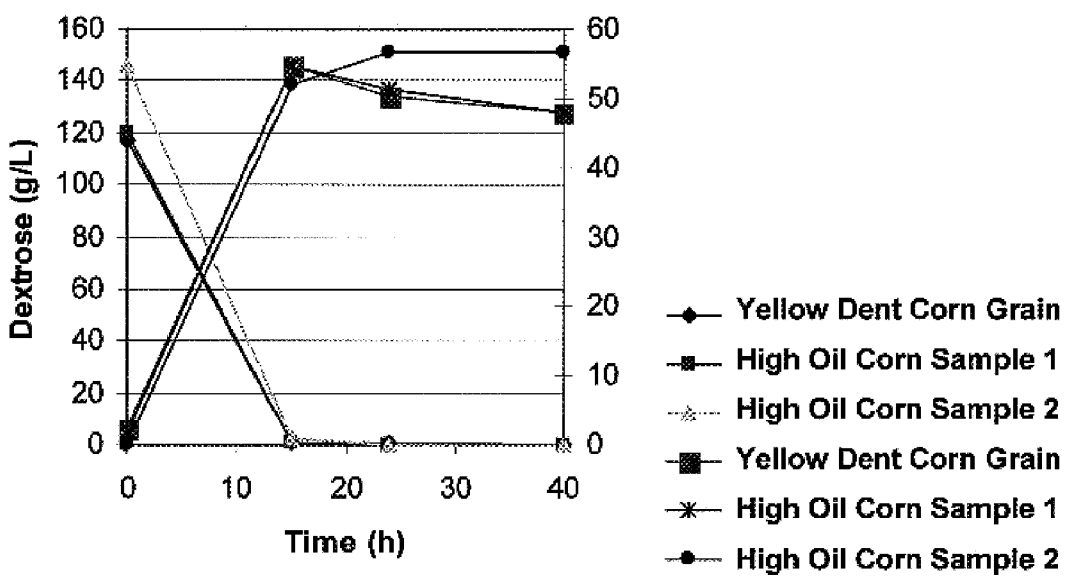
FIG. 4 shows the total amount of ethanol produced and dextrose consumed by yeast grown on dry-milled yellow dent and high oil corn grain samples with equal starch.
Figure 5:
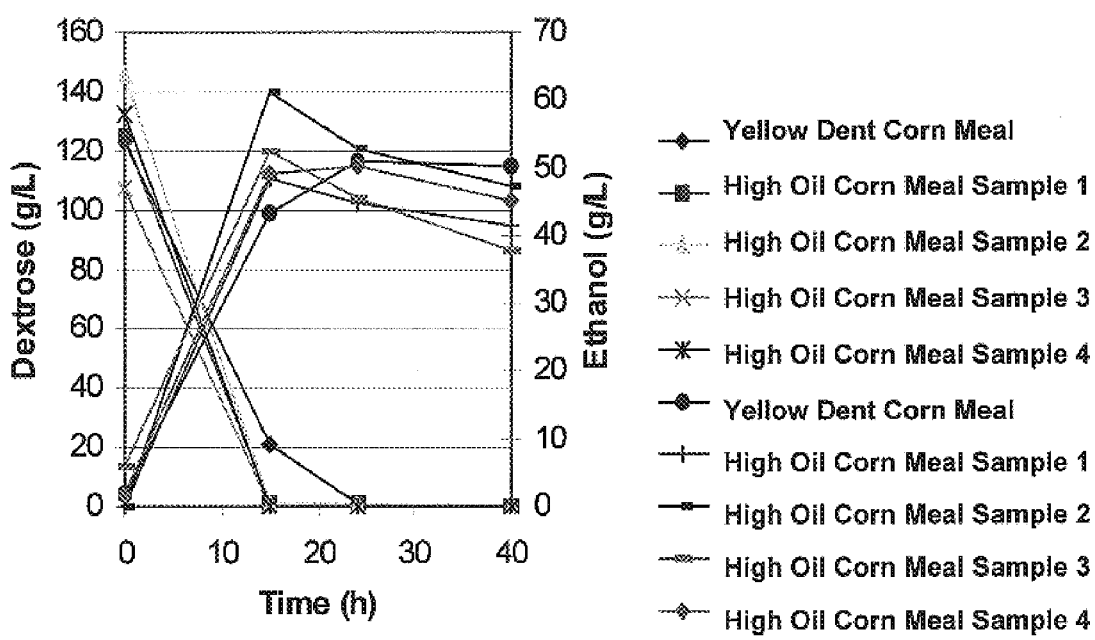
FIG. 5 illustrates the total amount of ethanol produced and dextrose consumed by yeast grown on oil-extracted yellow dent corn meal and high oil corn meal samples with equal starch.

Starting dextrose concentrations for yeast cultures were equalized to approximately 120 g/L. Yeast grown on yellow dent corn grain and high oil corn grain samples 1 and 2 utilized dextrose and produced ethanol at similar rates, as shown in FIG. 4. Conversely, yeast samples with corn meal samples displayed more variability in dextrose consumption and ethanol production, as displayed in FIG. 5 and Table 17. High oil corn meal sample 2 produced the most ethanol with the quickest rate, however, the starting dextrose was considerably higher than the other samples (>140 g/L).

Figure 6:
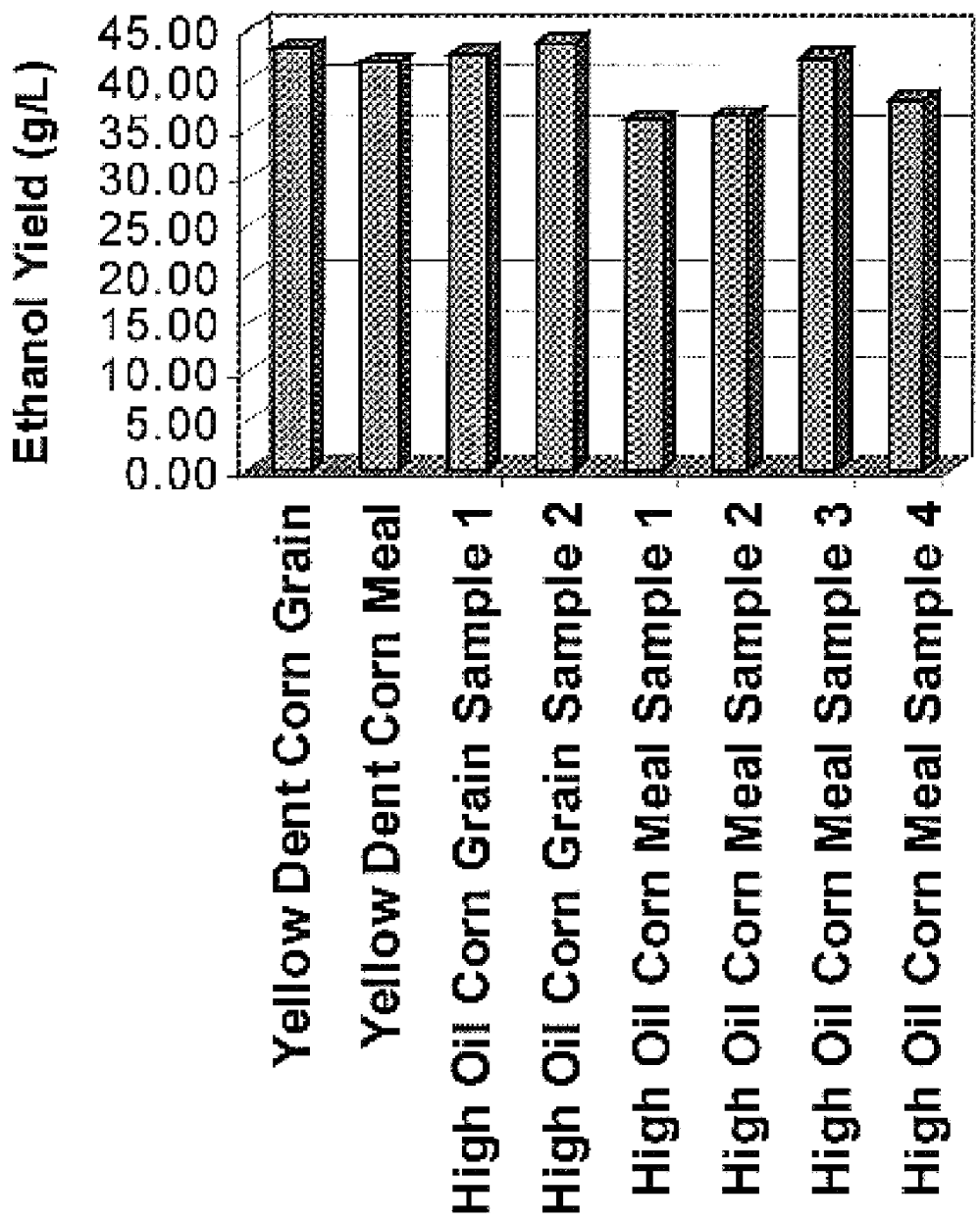
FIG. 6 displays the ethanol yields after 24 h of yeast grown on corn samples with equalized weight.

Yeast grown on grain samples displayed analogous ethanol yields after 24 h, as displayed in the chart of FIG. 6.

Yeast samples with high oil corn grain sample 1 and high oil corn grain sample 2 showed similar ethanol productivity values to samples with yellow dent after 15 h and after 24 h.

TABLE 17

| Fermentation media with: | Ethanol Productivity (g/L/h) | |
| --- | --- | --- |
| | 15 h | 24 h |
| Yellow Dent Corn Grain | 3.50 | 2.00 |
| High Oil Corn Grain 1 | 3.51 | 2.06 |
| High Oil Corn Grain 2 | 3.47 | 2.36 |
| High Oil Corn Meal 1 | 3.23 | 1.87 |
| High Oil Corn Meal 2 | 4.09 | 2.20 |

EXAMPLE 10

Production of Fermentation-Based Products

This example sets forth the use of solvent extracted corn meal from the current invention as a rich source of starch for the fermentative production of citric acid. The production of citric acid from de-fatted corn meal involves several steps including starch hydrolysis, fermentation, and citric acid recovery.

(A) Starch Hydrolysis

Solvent extracted corn meal of the present invention prepared as described herein is a rich source of starch for fermentation. One method to provide soluble sugars suitable for fermentation is to hydrolyze starch molecules. Types of enzymes that can be useful to convert the starch and protein matrix of corn meal into simple sugars suitable for fermentation include amylase(s), proteases, cellulase(s) (e.g., xylonase), esterase(s) (e.g., ferulase, acetylesterase) and ligninase(s).

Six samples (i.e., one sample of yellow dent corn grain (oil content 3.7%), one sample of yellow dent corn meal (0.3% oil), two samples of high oil corn grain (Grain 1 8.7% oil, Grain 2 12.5% oil and two samples of extracted high oil corn meal) (Meal 1 having 1.6% oil, Meal 2 having 1.9% oil) were ground to pass through a 1 mm screen using a Retsch Mill. Three hundred grams (300 g) of each sample was combined with 700 ml of water at 99° C.–100° C. comprising 0.5 ml α-amylase and placed in a sealed container. The pH of each mixture was adjusted to 5.9 with base. Each mixture was stirred for 45 min and additional α-amylase enzyme was added.

After an additional 45 min of incubation, the pH of each mixture was adjusted to 4.5 with acid. One-half of one milliliter (0.5 ml) glucoamylase (Optimax 7525) and 0.5 g protease (Fungal Protease 5000) were added to the sample mixtures and incubated with both enzymes at 62° C. or 22–24 h. Throughout the procedure, the degree of starch hydrolysis was monitored by HPLC (Waters 2690 Separations module) using an organic acid column (Aminex HPX-87H Ion Exclusion Column, 300 mm×7.8 mm, Bio Rad).

Total nitrogen content for each sample was determined by Leco 2000 CN. Free amino nitrogen (FAN) was determined by the AOAC method (15$^{th}$ Ed., 1990, p. 735). The amount of dextrose liberated from starch by the milling process and the amount of available nitrogen in the corn samples is set forth in Table 18.

TABLE 18

| Corn Sample | Calculated Initial Dextrose Content (g/L)♥ | Dextrose* (g/L) | Percent Starch Hydrolysis | FAN* (ppm) | Total Nitrogen (ppm)* |
| --- | --- | --- | --- | --- | --- |
| Yellow Dent Corn Grain | 251.94 | 175.6 | 69.70 | 223.8 | 2992 |
| Yellow Dent Corn Meal | 265.30 | 220.8 | 83.2 | 243.8 | 3392 |
| High Oil corn Grain 1 | 208.7 | 169.3 | 81.1 | 356.6 | 4288 |
| High Oil Corn Grain 2 | 208.8 | 150.6 | 72.1 | 339.0 | 4624 |
| High Oil Corn Meal 1 | 226.80 | 208.4 | 91.89 | 398.7 | 5920 |
| High Oil Corn Meal 2 | 242.1 | 180.5 | 74.6 | 436.3 | 5296 |

♥calculated based on starch content and a chemical gain of 1.11
*indicated "as is" values obtained from 30% starch hydrolysate The efficiency of starch hydrolysis varied among the different corn samples. High oil corn meal sample 1 exhibited at least 90% starch hydrolysis, which was the most efficient hydrolysis in this experiment. Yellow dent corn grain exhibited the least efficient starch hydrolysis, with a yield of 175.6 g/L dextrose obtained after hydrolysis of 251.94 g/L of dextrose.

High oil corn meal samples exhibited the highest average free amino nitrogen (FAN) and total nitrogen values. High oil corn grain samples displayed slightly less FAN and total nitrogen than corresponding meal, whereas yellow dent corn grain exhibited significantly lower results for free amino nitrogen and total nitrogen. As shown in Table 18, all high oil corn (grain and meal) samples contain a higher amount of nitrogen than their yellow dent (grain and meal) counterparts. Higher nitrogen levels could be due to higher initial protein in the high oil samples or higher susceptibility to protease treatment as compared to the yellow dent corn samples. The milling procedure was consistent for all samples with weight losses due to evaporation maintained from 3% to 5%.

(B) Fermentation and Citric Acid Production

Once the starch from solvent extracted corn meal is suitably prepared through treatment with enzymes, the solution is filtered and demineralized according to commonly known practices. Resulting sugars are brought to a solids content of about 120 mg/l with demineralized water in a deep-tank fermentation vessel. The deep tank method is also known as the submerged process. In this method the tank is supplied with sterile air, nutrients and a carbon source, (hydrolyzed starch), and inoculated with *Aspergillus niger* spores. Spores of the fungus in a concentration of about 100 spores per liter of culture liquid, which corresponds to an amount of 10 to 15 g of spores per cubic meter (m$^3$) would be added to the nutrient solution and the citric acid production would be carried out by the fungus. Examples of *A. niger* strains are ATCC 1015 described in U.S. Pat. No. 2,492,667, and DSM 5484 described in U.S. Pat. No. 5,081,025.

The incubation of the broth thus inoculated would be carried out at conditions generally known and described for citric acid production, such as continued aeration and temperature control. During the fermentation process, the temperature would be maintained at about 32° C. (90° F.), the pH would be maintained at about 2 to 3 with sodium citrate, and sterile air would be added to maintain about 50% dissolved oxygen content. Fermentation would be carried out until the fermentation broth reaches a reducing sugar content of about 1 g/L, which may require several days to achieve. Two main separation processes can be used in the recovery of citric acid, the Lime-Sulfuric Acid process and the Liquid extraction process. The Lime-Sulfuric Acid method is commonly used and is familiar to those skilled in the art of citric acid production.

EXAMPLE 11

Biodiesel Comprised of Corn Oil Derived From High Oil Corn

This example sets forth the use of oil from high oil corn as a source of an improved biodiesel fuel.

In a continuous process, approximately 62 kg/h (137 lbs/h) of oil extracted from high oil corn and refined according to known industry processes, is mixed with 18 kg/h (40 lbs/h) of methanol in a stirred tank reaction unit. Simultaneously, 0.08 kg/h (0.1775 lbs/h) of sodium hydroxide is added to the same stirred tank reaction unit, which operated at 20 psig and approximately 80° C. These conditions provide essentially 100% conversion of added triglycerides to fatty acids and methyl esters.

The two phases of the reaction mixture are allowed to stand and separate to provide methyl esters in the upper phase and a mixture of glycerol and approximately 10–15 percent by weight residual methyl esters, methanol, and base in the lower phase. Approximately 6.4 kg/h (14 lbs/h) of the glycerol phase is neutralized, present methanol flashed off, and the remainder is sent to a continuously stirred reaction unit, operated at 80° C. and 320 psig. The reaction unit also contains approximately 4 percent by weight Amberlyst-15 catalyst with a residence time of 2 h and approximately 7.9 kg/h (17.5 lbs/h) iso-butylene is fed to the reaction unit. The biodiesel fuel is produced at approximately 66 kg/h (145 lbs/h) and has a kinematic viscosity and cloud-point that is greater than biodiesel without glycerol ethers present.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of producing fermentation-based products comprising:
   (a) combining an enzyme, water, and a corn meal produced from high oil corn grain, wherein the oil has been extracted from the high oil corn grain;
   (b) incubating the combination; and
   (c) mixing the combination with a micro-organism capable of fermenting a carbon source to produce fermentation-based products.

2. The method of claim 1 wherein the enzyme is selected from the group consisting of an amylase, a protease, a cellulase, an esterase and a liginase.

3. The method of claim 2, wherein the enzyme is an amylase.

4. The method of claim 3, wherein the amylase enzyme is α-amylase.

5. The method of claim 2, wherein the enzyme is a cellulase.

6. The method of claim 5, wherein the cellulase enzyme is xylonase.

7. The method of claim 2, wherein the enzyme is an esterase.

8. The method of claim 7, wherein the esterase enzyme is selected from the group consisting of ferulase and acetylesterase.

9. The method of claim 2, wherein the enzyme is a protease.

10. The method of claim 2, wherein the additive is a ligninase.

11. The method of claim 1, wherein the whole high oil corn has an oil content of about 6 percent by weight or greater.

12. The method of claim 11, wherein the whole high oil corn has an oil content of from about 7 percent by weight to about 30 percent by weight.

13. The method of claim 11, wherein the whole high oil corn is tempered prior to extraction of the oil.

14. The method of claim 13, wherein the tempered corn is cracked prior to extraction of the oil.

15. The method of claim 14, wherein the cracked corn is flaked prior to extraction of the oil.

16. The method of claim 14, wherein the cracked corn is conditioned prior to extraction of the oil.

17. The method of claim 1, wherein the fermentation-based product is ethanol.

18. The method of claim 1, wherein the fermentation based product is citric acid.

19. The method of claim 1, wherein the extraction is accomplished by extracting corn oil using a continuous solvent extraction process.

20. The method of claim 16, wherein the grain remains in contact with the solvent for a time sufficient to extract the desired amount of oil.

21. The method of claim 17, wherein the corn remains in contact with the solvent for at least 10 minutes.

* * * * *